United States Patent
Bilodeau et al.

(10) Patent No.: US 9,480,657 B2
(45) Date of Patent: Nov. 1, 2016

(54) CABAZITAXEL-PLATINUM NANOPARTICLES AND METHODS OF USING SAME

(71) Applicant: TARVEDA THERAPEUTICS, INC., Watertown, MA (US)

(72) Inventors: Mark T. Bilodeau, Concord, MA (US); Craig A. Dunbar, Needham, MA (US); Timothy E. Barder, Arlington, MA (US); Edward R. Lee, Sudbury, MA (US); Rossitza G. Alargova, Brighton, MA (US); Danielle N. Rockwood, Medford, MA (US)

(73) Assignee: Tarveda Therapeutics, Inc., Watertown, MA (US)

( * ) Notice: Subject to any disclaimer, the term of this patent is extended or adjusted under 35 U.S.C. 154(b) by 0 days.

(21) Appl. No.: 14/216,127

(22) Filed: Mar. 17, 2014

(65) Prior Publication Data
US 2014/0378427 A1    Dec. 25, 2014

Related U.S. Application Data

(60) Provisional application No. 61/792,665, filed on Mar. 15, 2013.

(51) Int. Cl.
*A61K 47/48* (2006.01)
*A61K 9/51* (2006.01)
*A61K 31/337* (2006.01)
*A61K 33/24* (2006.01)

(52) U.S. Cl.
CPC ............ *A61K 9/5153* (2013.01); *A61K 31/337* (2013.01); *A61K 47/481* (2013.01); *A61K 33/24* (2013.01)

(58) Field of Classification Search
CPC ................... A61K 47/48076; A61K 31/337; A61K 9/5153
USPC ........................................ 514/185; 549/211
See application file for complete search history.

(56) References Cited

U.S. PATENT DOCUMENTS 6,340,770 B1    1/2002   Kwon et al.
2011/0257261 A1  10/2011  Lippard et al.

FOREIGN PATENT DOCUMENTS

WO    2011/143201 A2    11/2011

OTHER PUBLICATIONS

Walkey, C.D., et al., "Nanoparticle Size and Surface Chemistry Determine Serum Protein Adsorption and Macrophage Uptake," J. Am. Chem. Soc. 2012, 134, 2139-2147.
Perry, J.L., et al., "PEGylated PRINT Nanoparticles: The Impact of PEG Density on Protein Binding, Macrophage Association, Biodistribution, and Pharmacokinetics," Nano Lett 2012, 12, 5304-5310.
Morales-Cruz, M., et al., "Two-step nanoprecipitation for the production of protein-loaded PLGA nanospheres," Results in Pharma Sciences 2 (2012) 79-85.
Aryal et al.; "Nanoparticle drug delivery enhances the cytotoxicity of hydrophobic-hydrophilic drug conjugates;" J. Mater. Chem.; 22; pp. 994-999; 2012.

*Primary Examiner* — Kristin Vajda
(74) *Attorney, Agent, or Firm* — DT Ward, PC; Donna T. Ward; Heng Zhu

(57) ABSTRACT

The present teachings relate to compounds and compositions for treatment of cancers. In some embodiments, the composition comprises a platinum compound having a heterocycle ligand. Cabazitaxel-platinum nanoparticles are disclosed herein, as well as methods of making and using the same.

13 Claims, 1 Drawing Sheet

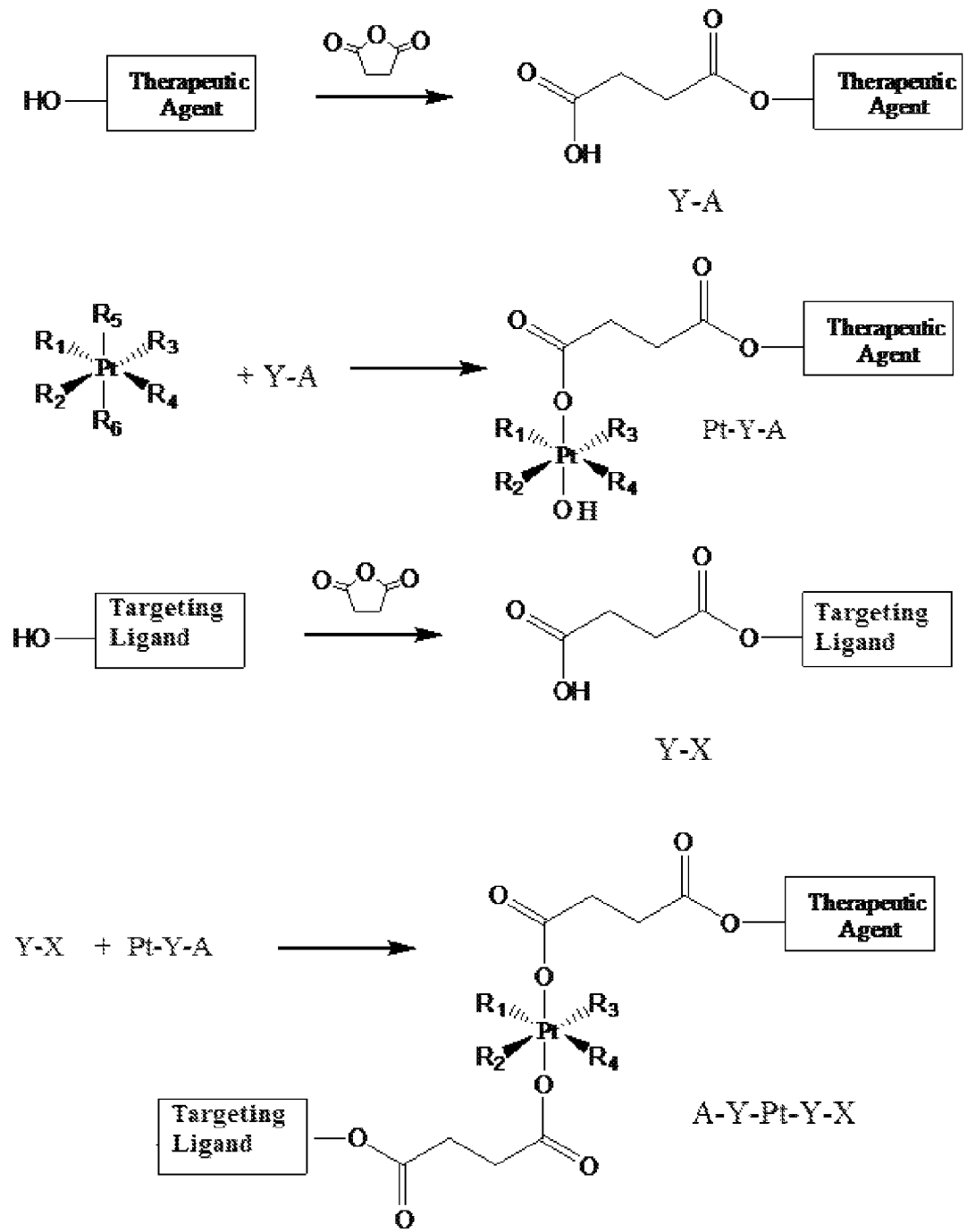

CABAZITAXEL-PLATINUM NANOPARTICLES AND METHODS OF USING SAME

CROSS REFERENCE TO RELATED APPLICATIONS

This application claims benefit of U.S. Provisional Patent Application No. 61/792,665 filed on Mar. 15, 2013; the disclosure of which is hereby incorporated by reference in its entirety.

FIELD

The present disclosure relates to pharmaceutical compositions comprising an active pharmaceutical agent linked to a platinum compound, and nanoparticles comprising such compounds. For example, the disclosure relates to cabazitaxel-platinum (IV) nanoparticles and methods of using and making the same.

BACKGROUND

Cabazitaxel is a semi-synthetic taxane of the formula (I).

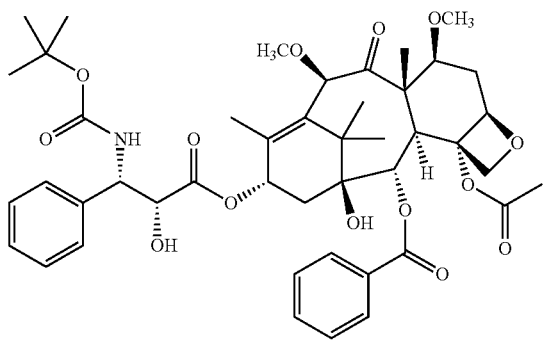

(I)

It is commercially available as an intravenous injection for the treatment of certain cancers (JEVTANA®, Sanofi-Aventis U.S. LLC). Several patents describe its composition and use. See, e.g., U.S. Pat. Nos. 5,438,072; 5,698,582; 5,847,170; 6,331,635; 6,372,780; 6,387,946; and 7,241,907. The U.S. Food and Drug Administration (FDA) approved the use of cabazitaxel in combination with prednisone for the treatment of metastatic hormone-refractory prostate cancer in 2010. Therapy employing cabazitaxel has been associated with a number of adverse reactions such as neutropenia, febrile neutropenia, severe hypersensitivity, gastrointestinal symptoms, renal failure, and hepatic impairment. Therefore, there is a need for improved cabazitaxel compositions to mitigate these adverse effects.

Platinum-containing drugs are used in some cancer therapies. Examples of such platinum drugs are cisplatin, carboplatin, and oxaliplatin, which are used clinically in the United States and elsewhere. The use of platinum(II) drugs in the treatment of malignancies has been somewhat limited because of the side effects and resistance acquired by cancer cells. An alternative to platinum(II) drug candidates is the use of substitutionally more inert platinum(IV) compounds as prodrugs derived from clinically effective platinum(II) compounds. Substitutionally inert platinum(IV) complexes are less likely to be deactivated prior to reaching their destination target in the cancer cell. The activity of platinum (IV) complexes generally involves reduction with concomitant loss of the axial ligands, affording an active platinum(II) complex that readily binds to DNA. The axial ligands that are released from the platinum(IV) complex may comprise a therapeutically active agent.

Some developments in nanomedicine are directed towards improving the pharmaceutical properties of drugs and creating or enhancing their targeted delivery in a cell-specific manner. Several cell-specific drugs are reported in literature, and include monoclonal antibodies, aptamers, peptides, and small molecules. Despite some potential advantages of these drugs, disadvantages have limited their clinical application. Such disadvantages include size, stability, manufacturing cost, immunogenicity, poor pharmacokinetics and other factors.

Nanoparticulate drug delivery systems are attractive for systemic drug delivery because of their potential to prolong drug circulation half-life, reduce non-specific uptake, and better accumulate at the tumors through an enhanced permeation and retention (EPR) effect. Several therapeutic nanoparticles such as Doxil® and Abraxane® are used as the frontline therapies.

The development of nanotechnologies for effective delivery of drugs or drug candidates to specific diseased cells and tissues, e.g., to cancer cells, in specific organs or tissues, in a tempospatially regulated manner can potentially overcome the therapeutic challenges faced to date. Accordingly, there is a need in the art for improved drug targeted conjugates utilizing targeting ligands with therapeutically active agents. It would be beneficial to link the therapeutic active drug to a platinum(IV) precursor and encapsulate this formulation in a nanoparticle.

SUMMARY

The present disclosure relates to novel pharmaceutical compositions comprising an active pharmaceutical agent, such as a chemotherapeutic agent, linked to a platinum complex. The active agent can be released from a nanoparticle in a controlled fashion. Typically, the platinum complex is also converted to a therapeutically active form. Also provided are methods of making a nanoparticle, as well as methods for using them in the treatment or prevention of diseases or conditions. The subject matter of the present disclosure involves, in some cases, interrelated products, alternative solutions to a particular problem, and/or a plurality of different uses of one or more systems and/or articles.

In various embodiments, the disclosure includes a nanoparticle, comprising an inner portion and an outer surface, the inner portion comprising a conjugate of a platinum complex connected to or associated with a targeting ligand and an active agent by linkers, wherein the conjugate has the formula:

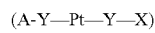

wherein:
X is a targeting ligand;
Y is a linker;
Pt is a platinum complex; and
A is a pharmaceutically active agent.

In one embodiment, the nanoparticles may contain a plurality of the same $(A-Y-Pt-Y-X)_n$ conjugates, or a plurality of conjugates wherein $(A-Y-Pt-Y-X)_n$ are different. In another embodiment, the platinum compound may be conjugated to two or more pharmaceutically active agents and two or more ligands wherein the conjugate has the formula: (A-Y)$_n$—Pt—(Y—X). In yet another embodiment, the platinum complex may be conjugated to two or more pharmaceutically active agents wherein the conjugate has the formula: (A-Y)$_n$—Pt—Y—X. In a further embodiment, the platinum complex may be conjugated to two or more ligands wherein the conjugate has the formula: A-Y—Pt—(Y—X)$_n$. n is an integer equal to or greater than 1. In one embodiment, the nanoparticles may contain a combination of some or all the above embodiments.

In another embodiment, the nanoparticles may contain a conjugate of a platinum complex and an active agent connected by a linker, wherein the conjugate has the formula: A-Y—Pt.

In another embodiment, the platinum compound may be conjugated to two or more active agents wherein the conjugate has the formula: (A-Y)$_n$—Pt. In a further embodiment, one active agent molecule may be linked to two or more platinum compounds wherein the conjugate has the formula: A-(Y—Pt)$_n$. In yet another embodiment, the nanoparticles may contain a plurality of the same (A-Y—Pt)$_n$ conjugates, or a plurality of conjugates wherein (A-Y—Pt)$_n$ are different. n is an integer equal to or greater than 1.

In one embodiment, X can be a peptide, antibody mimetic, nucleic acid (e.g. aptamer), polypeptide (e.g. antibody or its fragment), glycoprotein, small molecule, carbohydrate, or lipid. In another embodiment, X can be a peptide such as somatostatin, octeotide, EGF or RGD-containing peptides; an aptamer being either RNA or DNA or an artificial nucleic acid; small molecules; carbohydrates such as mannose, galactose and arabinose; vitamins such as ascorbic acid, niacin, pantothenic acid, carnitine, inositol, pyridoxal, lipoic acid, folic acid (folate), riboflavin, biotin, vitamin B$_{12}$, vitamin A, E, and K; a protein such as thrombospondin, tumor necrosis factors (TNF), annexin V, interferons, angiostatin, endostatin, cytokines, transferrin, GM-CSF (granulocyte-macrophage colony-stimulating factor), or growth factors such as vascular endothelial growth factor (VEGF), hepatocyte growth factor (HGF), platelet-derived growth factor (PDGF), basic fibroblast growth factor (bFGF), and epidermal growth factor (EGF).

In yet another embodiment, X can be RGD peptide, folic acid or prostate specific membrane antigen (PSMA).

In various aspects, Y is a linker bound to an active agent and a targeting ligand to form a conjugate wherein the conjugate releases at least one active agent upon delivery to a target cell. In one embodiment, the linker can be a $C_1$-$C_{10}$ straight chain alkyl, $C_1$-$C_{10}$ straight chain O-alkyl, $C_1$-$C_{10}$ straight chain substituted alkyl, $C_1$-$C_{10}$ straight chain substituted O-alkyl, $C_4$-$C_{13}$ branched chain alkyl, $C_4$-$C_{13}$ branched chain O-alkyl, $C_2$-$C_{12}$ straight chain alkenyl, $C_2$-$C_{12}$ straight chain O-alkenyl, $C_3$-$C_{12}$ straight chain substituted alkenyl, $C_3$-$C_{12}$ straight chain substituted O-alkenyl, polyethylene glycol, polylactic acid, polyglycolic acid, poly(lactide-co-glycolide), polycarprolactone, polycyanoacrylate, ketone, aryl, heterocyclic, succinic ester, amino acid, aromatic group, ether, crown ether, urea, thiourea, amide, purine, pyrimidine, bypiridine, indole derivative acting as a cross linker, chelator, aldehyde, ketone, bisamine, bis alcohol, heterocyclic ring structure, azirine, disulfide, thioether, hydrazone and combinations thereof. For example, the linker can be a $C_3$ straight chain alkyl or a ketone.

In one embodiment, A can be a chemotherapeutic agent, antibiotic, antimicrobial, growth factor and combinations thereof. In another aspect, A may be cabazitaxel or analogues or derivatives thereof.

In one embodiment, Pt is any platinum complex. In another embodiment, Pt is cisplatin ([cis-Pt(NH$_3$)$_2$Cl$_2$]), carboplatin ([cis-Pt(NH$_3$)$_2$(1,1-(OCO)C$_4$H$_6$)]), oxaliplatin, [cis-Pt(NH$_3$)$_2$(trans-1,2-(OCO)$_2$C$_6$H$_{10}$)], [cis-Pt(DACH)Cl$_2$] (where DACH is diaminocyclohexane), nedaplatin ([cis-Pt(NH$_3$)$_2$OCH$_2$CHO$_2$], stratoplatin, paraplatin, platinol, cycloplatam, dexormaplatin, enloplatin, iproplatin, lobaplatin, ormaplatin, spiroplatin, zeniplatin, etc., or any other derivative or salt thereof, as will be known to those of ordinary skill in the art.

In some embodiments, A is selected from a biomolecule, bioactive agent, small molecule, drug, prodrug, drug derivative, protein, peptide, vaccine, adjuvant, imaging agent (e.g., a fluorescent moiety) or polynucleotide.

In one embodiment, a cabazitaxel-platinum(IV) monohexanoate-monosuccinate conjugate of Formula (II) is provided as follows:

(II)

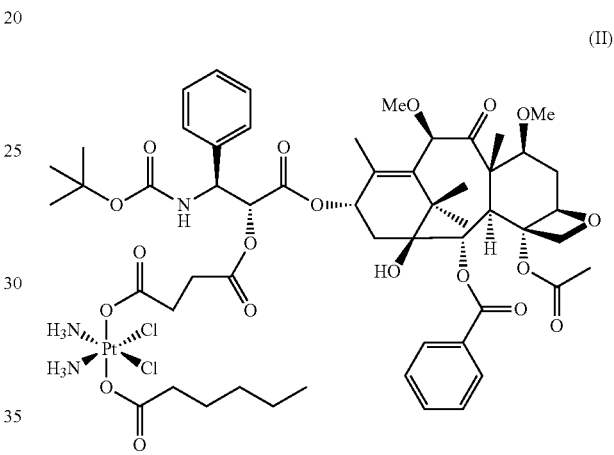

In one aspect, described herein are triple-targeted drug conjugates, which provide methods for active molecular targeting employing a bioactivated prodrug with enhanced permeability and retention effect (EPR) and improved overall biodistribution. Without limiting the teachings of the present disclosure, "triple-targeted" refers to a nanoparticulate composition comprising (1) one or more targeting ligands that bind to a target cell; (2) one or more pharmaceutically active agents linked in a prodrug form to the ligand that treats or modulates a disease or condition at the target cell; and (3) at least one polymer encapsulating all or part of the conjugate of the active agent and the ligand, wherein due to the EPR effect, the nanoparticle accumulates in the target tissue to be differentially retained while the active agent is released.

The conjugates taught herein may be formulated as nanoparticles. In some embodiments they are encapsulated, in whole or in part, in the inner portion of the nanoparticles. The nanoparticles may have a substantially spherical or non-spherical configuration (e.g., upon swelling or shrinkage). The nanoparticles may include polymer blends. In various embodiments, the base component of the nanoparticles comprises a polymer, a small molecule, or a mixture thereof. The base component can be biologically derived. For example, the small molecule can be, for example, a lipid. A "lipid," as used herein, refers to a hydrophobic or amphiphilic small molecule. Without attempting to limit the scope of the present teachings, lipids, because of their amphiphilicity, can form particles, including liposomes and micelles.

The base component may be a cyclodextrin or an inorganic platform useful in forming nanoparticles.

In another embodiment, a pharmaceutical composition is provided comprising the nanoparticulate conjugates described herein, or pharmaceutically acceptable salts thereof, in a pharmaceutically acceptable vehicle. For example, an isotonic solution suitable for intravenous injection is contemplated by the present disclosure. In other embodiments, the compositions are formulated as oral, subcutaneous or intramuscular dosage forms.

In yet another embodiment, the conjugates are released from the nanoparticle in a controlled fashion. Also contemplated are methods of making the nanoparticles, as well as methods for using them in the treatment or prevention of diseases or conditions.

In a further embodiment, a method is provided for treating a disease or condition, the method comprising administering a therapeutically effective amount of the nanoparticles to a subject in need thereof. In one aspect, the disease is a cancer or proliferative disease, for example, lymphoma, renal cell carcinoma, leukemia, prostate cancer, lung cancer, pancreatic cancer, melanoma, colorectal cancer, ovarian cancer, breast cancer, glioblastoma multiforme and leptomeningeal carcinomatosis.

Other embodiments, objects, features, and advantages will be set forth in the detailed description of the embodiments that follow and, in part, will be apparent from the description or may be learned by practice of the claimed invention. These objects and advantages will be realized and attained by the compositions and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

The invention is described below in connection with the following illustrative FIGURE, and wherein:

FIG. 1 is the generic scheme for the synthesis of the drug-linker-platinum compound-linker-targeting ligand conjugates and their nano-encapsulation.

DETAILED DESCRIPTION

While the present disclosure is capable of being embodied in various forms, the description below of several embodiments is made with the understanding that the present disclosure is to be considered as an exemplification of the claimed subject matter, and is not intended to limit the appended claims to the specific embodiments illustrated and/or described, and should not be construed to limit the scope or breadth of the present disclosure. The headings used throughout this disclosure are provided for convenience only and are not to be construed to limit the claims in any way. Embodiments illustrated under any heading may be combined with embodiments illustrated under any other heading.

I. Definitions

For convenience, before further description of the present teachings, certain terms employed in the specification, examples, and appended claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

A. General Terms

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of", when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," "associated," "associated with," and the like are to be understood to be open-ended, i.e. to mean including but not limited to.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

B. Terms Related to Compositions of the Present Disclosure

A "target" shall mean a site to which a targeted construct can bind. A target may be either in vivo or in vitro. In certain embodiments, a target may be a cancer cell found in a leukemia or tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis)) and pathogenic fungi (e.g., *Candida* sp.). Certain target infectious organisms include those that are drug resistant (e.g., Enterobacteriaceae, *Enterococcus, Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety or ligand binds, such as a hapten, epitope, receptor, dsDNA fragment, carbohydrate or enzyme. Additionally, a target may be a type of tissue, e.g., neuronal tissue, intestinal tissue, pancreatic tissue etc.

A "target cell," which may serve as the target for the method or coordination complexes of the present disclosure, include prokaryotes and eukaryotes, including yeasts, plant cells and animal cells. The present method may be used to modify cellular function of living cells in vitro, i.e., in cell culture, or in vivo, in which the cells form part of or otherwise exist in plant tissue or animal tissue. Thus, the target cells may include, for example, the blood, lymph tissue, cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject disclosure), dermal/epidermal cells, cells of the vagina and rectum, cells of internal organs including cells of the placenta and the so-called blood/brain barrier, etc.

"Targeting ligand" or "targeting moiety" are used interchangeably and shall include a peptide, antibody mimetic, nucleic acid (e.g. aptamer), polypeptide (e.g. antibody), glycoprotein, small molecule, carbohydrate, or lipid.

As used herein, the term "linker" refers to a carbon chain that can contain heteroatoms (e.g., nitrogen, oxygen, sulfur, etc.) and which may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted. Examples of linkers include, but are not limited to, pH-sensitive linkers, protease cleavable peptide linkers, nuclease sensitive nucleic acid linkers, lipase sensitive lipid linkers, glycosidase sensitive carbohydrate linkers, hypoxia sensitive linkers, photo-cleavable linkers, heat-labile linkers, enzyme cleavable linkers (e.g., esterase cleavable linker), ultrasound-sensitive linkers, x-ray cleavable linkers, and so forth.

The terms "therapeutic agent" or "active agent" or "pharmaceutically active agent" are art-recognized and refer to an agent capable of having a desired biological effect on a host.

The term "nanoparticle" as used herein refers to a particle having a characteristic dimension of less than about 1 micrometer, where the characteristic dimension of a particle is the diameter of a perfect sphere having the same volume as the particle. A plurality of particles, e.g., nanoparticles, can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 50 nm, at least about 100 nm, at least about 150 nm, or greater. In certain embodiments, the plurality of the particles have an average diameter of about 10 nm, about 25 nm, about 50 nm, about 100 nm, about 150 nm, about 200 nm, about 250 nm, about 300 nm, about 500 nm, or the like. In some embodiments, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles have an average diameter between about 10 nm and about 500 nm, between about 20 nm and about 400 nm, between about 30 nm and about 300 nm, between about 40 nm and about 200 nm, between about 50 nm and about 175 nm, between about 60 nm and about 150 nm, between about 70 nm and about 120 nm, or the like. For example, the average diameter can be between about 70 nm and 120 nm.

C. Terms Related to Methods of Treatment

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or is a subject selected for treatment, observation, or experiment on the basis of a known cancer in the subject.

As used herein, "treatment" or "treating" refers to an amelioration of a disease or disorder, or at least one sign or symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, for example, by reducing the rate of disease progression compared to a reference population having the same disease or decreasing the degree or rate or progression of a sign or symptom in the subject prior to treatment. In yet another embodiment, "treatment" or "treating" refers to delaying the onset of a disease or disorder, e.g., compared to a reference population or other method of determining such a parameter as is known by those in the art.

As used herein, "prevention" or "preventing" refers to a reduction of the risk of acquiring a given disease or disorder.

The phrase "therapeutically effective amount" as used herein means that amount of a compound, material, or composition comprising a compound of the present teachings that is effective for producing a desired therapeutic effect. Accordingly, a therapeutically effective amount treats or prevents a disease or a disorder, ameliorates at least one sign or symptom of the disorder, e.g., slows the rate of advance of at least one sign or symptom. In various embodiments, the disease or disorder is a cancer.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human.

The term "modulation" is art-recognized and refers to up regulation (i.e., activation or stimulation), down regulation (i.e., inhibition or suppression) of a response, or the two in combination or apart.

The terms "systemic administration," "administered systemically," "peripheral administration" and "administered peripherally" are art-recognized and refer to the administration of a composition, therapeutic or other material other than directly into the central nervous system, such that it enters the patient's system and, thus, is subject to metabolism and other like processes, for example, intravenous or subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

D. Chemical Terms

A dash ("-") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as $(C_1-C_{22})$alkyl, $(C_1-C_8)$alkyl, $(C_1-C_6)$alkyl, and $(C_1-C_4)$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond (shown, for example, as "="), such as a straight or branched group of 2-22, 2-8, 2-6, or 2-4 carbon atoms, referred to herein as $(C_2-C_{22})$alkenyl, $(C_2-C_8)$alkenyl, $(C_2-C_6)$alkenyl, and $(C_2-C_4)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond (shown, for example, as "≡"), such as a straight or branched group of 2-22, 2-8, 2-6, 2-4 carbon atoms, referred to herein as $(C_2-C_{22})$alkynyl, $(C_2-C_8)$alkynyl, $(C_2-C_6)$alkynyl, and $(C_2-C_4)$alkynyl, respectively. Exemplary alkynyl groups include, but are not limited to, ethynyl, propynyl, butyryl, pentynyl, hexynyl, methylpropynyl, 4-methyl-1-butyryl, 4-propyl-2-pentynyl, and 4-butyl-2-hexynyl.

The term "cycloalkyl" as used herein refers to a saturated or unsaturated monocyclic, bicyclic, other multicyclic, or bridged cyclic hydrocarbon group. A cyclocalkyl group can have 3-22, 3-12, or 3-8 ring carbons, referred to herein as $(C_3-C_{22})$cycloalkyl, $(C_3-C_{12})$cycloalkyl, or $(C_3-C_8)$cycloalkyl, respectively. A cycloalkyl group can also have one or more carbon-carbon double bond or carbon-carbon triple bond.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle[3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as $(C_6-C_{22})$aryl, $(C_6-C_{18})$aryl, $(C_6-C_{14})$aryl, or $(C_6-C_{10})$aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocylic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl." The term "benzyl" as used herein refers to the group —CH$_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1,9-diamine, or the like.

The term "heteroaromatic" or "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "$(C_2-C_5)$heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl).

The term "bicyclic heteroaromatic" or "bicyclic heteroaryl" as used herein refers to a heteroaryl group fused to another aromatic or non-aromatic carbocylic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl).

The term "tricyclic heteroaromatic" or "tricyclic heteroaryl" as used herein refers to a bicyclic heteroaryl group fused to another aromatic or non-aromatic carbocylic or heterocyclic ring. The term "tricyclic heteroaromatic" or "tricyclic heteroaryl" also encompasses reduced or partly reduced forms of fused aromatic system wherein one or both rings contain ring heteroatoms. Each of the ring in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), pyrido[1,2-a]benzimidazole (pyrido[1,2-a]benzimidazolyl), and pyrido[1,2-b]indazole (pyrido[1,2-b]indazolyl).

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, or ($C_1$-$C_6$)alkoxy, respectively. Exemplary alkoxy groups include, but are not limited to methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy." The term "arylalkoxy" as used herein refers to an arylalkyl group attached to an oxygen atom. An exemplary aryalkyl group is benzyloxy group.

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R_{b'}$ is not hydrogen. The amine or amino can be attached to the parent molecular group through the nitrogen. The amine or amino also may be cyclic, for example any two of $R_a$, $R_b$, and $R_{b'}$ may be joined together and/or with the N to form a 3- to 12-membered ring (e.g., morpholino or piperidinyl). The term amino also includes the corresponding quaternary ammonium salt of any amino group. Exemplary amines include alkylamine, wherein at least one of $R_aR_b$, or $R_{b'}$ is an alkyl group, or cycloalkylamine, wherein at least one of $R_aR_b$, or $R_{b'}$ is a cycloalkyl group.

The term "ammonia" as used herein refers to $NH_3$.

The term "aldehyde" or "formyl" as used herein refers to —CHO.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —$NR_cC(O)(R_d)$— or —$C(O)NR_cR_e$, wherein $R_c$, $R_d$, and $R_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_c$, $R_d$, or $R_e$. The amide also may be cyclic, for example $R_c$ and $R_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "carbamate" as used herein refers to the form —$R_fOC(O)N(R_g)$—, —$R_fOC(O)N(R_g)R_h$—, or —$OC(O)NR_gR_h$, wherein $R_f$, $R_g$, and $R_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_f$, $R_g$ and $R_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to $R_j$—COOH or its corresponding carboxylate salts (e.g., $R_j$—COONa), where $R_j$, can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein $R_j$ is alkyl, such as —O—C(O)-alkyl. Exemplary carboxy also include aryl or heteroaryl carboxy, e.g. wherein $R_j$ is an aryl, such as phenyl and tolyl, or heteroaryl group such as pyridine, pyridazine, pyrmidine and pyrazine. The term carboxy also includes "carboxycarbonyl," e.g. a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—$R_i$—, —$R_j$C(O)O—$R_i$—, or —$R_j$C(O)O—, where O is not bound to hydrogen, and $R_i$, and $R_j$, can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_i$, can be a hydrogen, but $R_j$, cannot be hydrogen. The ester may be cyclic, for example the carbon atom and $R_j$, the oxygen atom and $R_i$, or $R_i$ and $R_j$ may be joined to form a 3- to 12-membered ring. Exemplary esters include, but are not limited to, alkyl esters wherein at least one of $R_i$ or $R_j$ is alkyl, such as —O—C(O)-alkyl, —C(O)—O-alkyl-, and -alkyl—C(O)—O-alkyl-. Exemplary esters also include aryl or heteroaryl esters, e.g. wherein at least one of $R_i$, or $R_j$ is an aryl group, such as phenyl or tolyl, or a heteroaryl group, such as pyridine, pyridazine, pyrimidine or pyrazine, such as a nicotinate ester. Exemplary esters also include reverse esters having the structure —$R_j$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_k$O—$R_l$—, where $R_k$ and $R_l$ can independently be alkyl, alkenyl, alkynyl, aryl, cycloalkyl, heterocyclyl, and ether. The ether can be attached to the parent molecular group through $R_k$ or $R_l$. Exemplary ethers include, but are not limited to, alkoxyalkyl and alkoxyaryl groups. Ethers also includes polyethers, e.g., where one or both of $R_k$ and $R_l$ are ethers.

The terms "halo" or "halogen" or "hal" or "halide" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_m$ (such as acetyl, —C(O)CH$_3$) or —$R_m$—C(O)—$R_n$—. The ketone can be attached to another group through $R_m$ or $R_n$. $R_m$ or $R_n$ can be alkyl, alkenyl, alkynyl, cycloalkyl, heterocyclyl or aryl, or $R_m$ or $R_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3^-$.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —$R_o$OP(O)O$_2^{2-}$, —OP(O)(OR$_q$)O$^-$, or —$R_o$OP(O)(OR$_p$)O$^-$, wherein $R_o$, $R_p$ and $R_q$ each independently can be alkyl, alkenyl, alkynyl, aryl, cycloalkyl, heterocyclyl, or hydrogen.

The term "sulfide" as used herein refers to the structure —$R_q$S—, where $R_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —$R_r$S(O)O—, —$R_r$S(O)OR$_s$—, or —S(O)OR$_s$—, wherein $R_r$ and $R_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_r$ or $R_s$ is alkyl, alkenyl, or alkynyl.

The term "sulfonamide" as used herein refers to the structure —(R$_t$)—N—S(O)$_2$—R$_v$— or —R$_t$(R$_u$)N—S(O)$_2$—R$_v$, where $R_t$, $R_u$, and $R_v$ can be, for example, hydrogen, alkyl, alkenyl, alkynyl, aryl, cycloalkyl, and heterocyclyl. Exemplary sulfonamides include alkylsulfonamides (e.g., where $R_v$ is alkyl), arylsulfonamides (e.g., where $R_v$ is aryl), cycloalkyl sulfonamides (e.g., where $R_v$ is cycloalkyl), and heterocyclyl sulfonamides (e.g., where $R_v$ is heterocyclyl).

The term "sulfonate" as used herein refers to a salt or ester of a sulfonic acid. The term "sulfonic acid" refers to $R_w$SO$_3$H, where $R_w$ is alkyl, alkenyl, alkynyl, aryl, cycloalkyl, or heterocyclyl (e.g., alkylsulfonyl). The term "sulfonyl" as used herein refers to the structure $R_x$SO$_2$—, where $R_x$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "sulfonate" as used herein refers $R_w$SO$_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, CF$_3$SO$_3^-$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_aR_bR_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the disclosure or the intermediates useful for preparing them. Examples of suitable substituents include, but are not limited to: ($C_1$-$C_{22}$), ($C_1$-$C_8$), ($C_1$-$C_6$), or ($C_1$-$C_4$) alkyl, alkenyl or alkynyl; ($C_6$-$C_{22}$), ($C_6$-$C_{18}$), ($C_6$-$C_{14}$), or ($C_6$-$C_{10}$) aryl; ($C_2$-$C_{21}$), ($C_2$-$C_{17}$), ($C_2$-$C_{13}$), or ($C_2$-$C_9$) heteroaryl; ($C_3$-$C_{22}$), ($C_3$-$C_{12}$), or ($C_3$-$C_8$) cycloalkyl; ($C_1$-$C_{22}$), ($C_1$-$C_8$), ($C_1$-$C_6$), or ($C_1$-$C_4$) alkoxy; ($C_6$-$C_{22}$), ($C_6$-$C_{18}$), ($C_6$-$C_{14}$), or ($C_6$-$C_{10}$) aryloxy; —CN; —OH; oxo; halo; carboxy; amino, such as —NH(($C_1$-$C_{22}$), ($C_1$-$C_8$), ($C_1$-$C_6$), or ($C_1$-$C_4$) alkyl), —N(($C_1$-$C_{22}$), ($C_1$-$C_8$), ($C_1$-$C_6$), or ($C_1$-$C_4$) alkyl)$_2$, —NH(($C_6$)aryl), or —N(($C_6$-$C_{10}$) aryl)$_2$; formyl; ketones, such as —CO(($C_1$-$C_{22}$), ($C_1$-$C_8$), ($C_1$-$C_6$), or ($C_1$-$C_4$) alkyl), —CO((($C_6$-$C_{10}$) aryl) esters, such as —CO$_2$(($C_1$-$C_{22}$), ($C_1$-$C_8$), ($C_1$-$C_6$), or ($C_1$-$C_4$) alkyl) and —CO$_2$(($C_6$-$C_{10}$) aryl). One of skill in art can readily choose a suitable substituent based on the stability and pharmacological and synthetic activity of the compound of the disclosure.

Unless otherwise specified, the chemical groups include their corresponding monovalent, divalent, trivalent, and tetravalent groups. For example, methyl includes monovalent methyl (—CH$_3$), divalent methyl (—CH$_2$—, methylyl), trivalent methyl

and tetravalent methyl

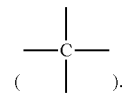

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

All numerical ranges herein include all numerical values and ranges of all numerical values within the recited range of numerical values. As a non-limiting example, $(C_1-C_6)$ alkyls also include any one of $C_1$, $C_2$, $C_3$, $C_4$, $C_5$, $C_6$, $(C_1-C_2)$, $(C_1-C_3)$, $(C_1-C_4)$, $(C_1-C_5)$, $(C_2-C_3)$, $(C_2-C_4)$, $(C_2-C_5)$, $(C_2-C_6)$, $(C_3-C_4)$, $(C_3-C_5)$, $(C_3-C_6)$, $(C_4-C_5)$, $(C_4-C_6)$, and $(C_5-C_6)$ alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

A "polymer," as used herein, is given its ordinary meaning as used in the art, i.e., a molecular structure comprising one or more repeating units (monomers), connected by covalent bonds. The repeating units may all be identical, or in some cases, there may be more than one type of repeating unit present within the polymer.

If more than one type of repeating unit is present within the polymer, then the polymer is said to be a "copolymer." It is to be understood that in any embodiment employing a polymer, the polymer being employed may be a copolymer in some cases. The repeating units forming the copolymer may be arranged in any fashion. For example, the repeating units may be arranged in a random order, in an alternating order, or as a "block" copolymer, i.e., comprising one or more regions each comprising a first repeating unit (e.g., a first block), and one or more regions each comprising a second repeating unit (e.g., a second block), etc. Block copolymers may have two (a diblock copolymer), three (a triblock copolymer), or more numbers of distinct blocks.

The term "hydrophilic," as used herein, generally describes the property of attracting water and the term "hydrophobic," as used herein, generally describes the property of repelling water. Thus, a hydrophilic compound (e.g., small molecule or polymer) is one generally that attracts water and a hydrophobic compound (e.g., small molecule or polymer) is one that generally repels water. A hydrophilic or a hydrophobic compound can be identified, for example, by preparing a sample of the compound and measuring its contact angle with water. In some cases, the hydrophilicity of two or more compounds may be measured relative to each other, i.e., a first compound may be more hydrophilic than a second compound.

E. Terms Related to Pharmaceutics

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, matate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the formulation and not injurious to the patient.

II. Composition of the Drug-Platinum Compound-Targeting Ligand Conjugates

The present teachings include active agent-platinum compound-targeting ligand conjugates, including nanoparticles thereof, pharmaceutical compositions, methods of producing such compositions and methods of using the same. In other aspects, the teachings provide methods for preparing drug delivery compositions, e.g., nanoparticles, such as polymers having pendant functional groups. One advantage of the present disclosure is that by engineering and blending distinct drug-functionalized and ligand-functionalized polymers, particles capable of delivering two, three, or more drugs can be reproducibly engineered and characterized. Additionally, these methods allow for characteristics of drug release and pharmacokinetics to be tuned for each type of agent and regardless of the characteristics of the active agents (i.e., solubility, charge, molecular weight, half-life, and/or biodistribution profiles). Further, by targeting drug-loaded particles to specific tissues or cells, e.g. cancer cells, synergistic drug effects can be achieved that can alter the biodistribution of active agents. This can translate to better efficiency and tolerability, making active agents suitable for potential clinical development.

In general, the compounds of the present disclosure may be prepared by the methods illustrated in the general reaction schema described below, or by modifications thereof, using readily available starting materials, reagents and conventional synthesis procedures. In these reactions, it is also possible to make use of variants which are in themselves known, but are not mentioned here.

In an embodiment, the invention relates to a conjugate of a platinum complex and an active agent connected by a linker, wherein the conjugate has the formula: A-Y—Pt.

In another embodiment, one platinum compound may be conjugated to two or more active agents wherein the conjugate has the formula: $(A-Y)_n$-Pt. In a further embodiment, one active agent molecule may be linked to two or more platinum compounds wherein the conjugate has the formula: $A-(Y—Pt)_n$. n is an integer equal to or greater than 1.

In various embodiments, the disclosure includes a nanoparticle, comprising an inner portion and an outer surface, the inner portion comprising a conjugate as described herein, e.g., of a platinum complex connected to a targeting ligand and an active agent by linkers, wherein the conjugate has the formula:

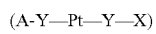

wherein:
X is a targeting ligand;
Y is a linker;
Pt is a platinum complex; and
A is a pharmaceutically active agent.

In one embodiment, the nanoparticles may contain a plurality of the same $(A-Y—Pt—Y—X)_n$ conjugates, or a plurality of conjugates wherein $(A-Y—Pt—Y—X)_n$ are different. In another embodiment, the two ligands may be conjugated to two or more pharmaceutically active agents and two or more ligands wherein the conjugate has the formula: $(A-Y)_n—Pt—(Y—X)_n$. In yet another embodiment, the platinum complex may be conjugated to two or more pharmaceutically active agents wherein the conjugate has the formula: $(A-Y)_n—Pt—Y—X$. In a further embodiment, the platinum complex may be conjugated to two or more ligands wherein the conjugate has the formula: A-Y-Pt-$(Y-X)_n$. n is an integer equal to or greater than 1. In one embodiment, the nanoparticles may contain a combination of some or all the above embodiments.

In another embodiment, a nanoparticle contains a conjugate as described herein, e.g., of a platinum complex and an active agent connected by a linker, wherein the conjugate has the formula: A-Y—Pt. In another embodiment, one platinum compound may be conjugated to two or more active agents wherein the conjugate has the formula: $(A-Y)_n$—Pt. In a further embodiment, one active agent molecule may be linked to two or more platinum compounds wherein the conjugate has the formula: $A-(Y—Pt)_n$. In yet another embodiment, the nanoparticles may contain a plurality of the same $(A-Y—Pt)_n$ conjugates, or a plurality of conjugates wherein $(A-Y—Pt)_n$ are different. n is an integer equal to or greater than 1.

In yet another embodiment of the present disclosure, the platinum compound may comprise at least one ligand which functions as a linker, and is selected such that the therapeutic agent or the targeting ligand is linked to the Pt compound, as discussed herein.

As detailed further below, X can be a targeting ligand selected from the group consisting of a peptide, antibody mimetic, nucleic acid (e.g. aptamer), polypeptide (e.g. antibody), glycoprotein, small molecule, carbohydrate, or lipid.

In various aspects, Y is a linker bound to the platinum compound and an active agent (A) and/or a targeting ligand (X) to form a conjugate wherein the conjugate releases at least one active agent upon delivery to a target cell.

In some embodiments, the active agent is selected from a biomolecule, bioactive agent, small molecule, drug, prodrug, drug derivative, protein, peptide, vaccine, adjuvant, imaging agent (e.g., a fluorescent moiety) or polynucleotide.

The generic scheme for the synthesis of the drug-linker-platinum compound-linker-targeting ligand conjugates and their nano-encapsulation is illustrated in FIG. 1.

Referring to FIG. 1, a conjugate of the present teachings may, in some embodiments, be prepared by: a) providing a therapeutically active agent having a hydroxyl group and reacting it with succinic anhydride to form the conjugate of active agent-succinate, b) reacting a platinum complex with a coupling reagent and the active agent-succinate to form the active agent-linker-platinum complex conjugate, c) providing a targeting ligand having a hydroxyl group and reacting it with succinic anhydride to form the conjugate of targeting ligand-succinate, and d) reacting the active agent-linker-platinum complex conjugate with a coupling agent and the targeting ligand-succinate to form targeting ligand-linker-platinum complex-linker-active agent conjugate.

In another embodiment, conjugates of the present teachings may, in some embodiments, be prepared by: a) providing a therapeutically active agent having a hydroxyl group and reacting it with succinic anhydride to form the conjugate of active agent-succinate, b) reacting a platinum complex with a coupling reagent and the active agent-succinate to form the active agent-linker-platinum complex conjugate.

In another embodiment, a pharmaceutical composition is provided comprising the nanoparticulate conjugates described herein, or pharmaceutically acceptable salts thereof, in a pharmaceutically acceptable vehicle. For example, an isotonic solution suitable for intravenous injection is contemplated by the present disclosure.

In certain embodiments, a platinum compound can be conjugated to one or more active agents and targeting ligands by a suitable chemical linker through environmentally cleavable bonds. Any of a variety of methods can be used to associate a linker with a pharmaceutically active agent including, but not limited to, passive adsorption (e.g., via electrostatic interactions), multivalent chelation, high affinity non-covalent binding between members of a specific binding pair, covalent bond formation, etc. In some embodiments, click chemistry can be used to associate a linker with a particle (e.g. Diels-Alder reaction, Huigsen 1,3-dipolar cycloaddition, nucleophilic substitution, carbonyl chemistry, epoxidation, dihydroxylation, etc.). In various aspects, conjugates are provided including a plurality of linkers each of which is bound to pharmaceutically active agents and targeting ligands wherein the conjugate releases the pharmaceutically active agent upon delivery to target cells.

Linkers can be cleaved in a variety of ways to release the active therapeutic agent. These include acidic hydrolysis, enzymatic hydrolysis and reductive processes. Some chemical bonds such as hydrazone, ester and amide bonds are sensitive to acidic pH values, for example, of the intracellular environment of tumor cells. At acidic pH, hydrogen ions catalyze the hydrolysis of these bonds which in turn releases the drug from its conjugate format. In the reducing environment of the cytoplasm of tumor cells some functional groups such as Pt(IV) complexes can be reduced to active Pt(II) complexes. Therefore, different pharmaceutically active agents, such as but not limited to cabazitaxel, platinum(IV) complexes, oxaliplatin, cisplatin, carboplatin, paclitaxel, docetaxel and the like having —OH, —NH$_2$, —SH, —COOH, alkenyl, phosphate, sulfate, heterocyclic NH, alkyne and/or ketonic groups may be covalently linked together with a suitable spacer with alkyl chains of variable lengths. These spacers may be introduced to the conjugates by reacting different acid anhydrides and any organic compounds having mono-functional or bifunctional or hetero functional groups with the active agents and targeting ligands.

The coupling reaction can be carried out under esterification conditions known to those of ordinary skill in the art such as in the presence of activating agents, e.g., carbodiimides (such as diisopropoylcarbodiimide (DIPC)), with or without catalyst such as dimethylaminopyridine (DMPA). This reaction can be carried our in an appropriate solvent, such as dichloromethane, chloroform or ethyl acetate, at a temperature or between about 0° C. and the reflux temperature of the solvent (e.g., ambient temperature).

In other aspects, where the linker is a disuccinate compound, the precursor employed is succinic anhydride. Where the linker is a diglycolate group, the precursor is diglycolic anhydride.

The coupling reaction is generally performed in a solvent such as pyridine or in a chlorinated solvent in the presence of a catalyst such as DMAP or pyridine at a temperature between about 0° C. and the reflux temperature of the solvent (e.g., ambient temperature). In one embodiment, the coupling reagent is selected from the group consisting of 4-(2-pyridyldithio)-butanoic acid, and a carbodiimide copling reagent such as DCC in a chlorinated, ethereal or amidic solvent (such as N,N-dimethylformamide) in the presence of a catalyst such as DMAP at a temperature between about 0° C. and the reflux temperature of the solvent (e.g., ambient temperature).

In various aspects, the variable "n" of the formula (A-Y—Pt—Y—X)$_n$, is an integer greater than or equal to 2. In various aspects, this numeral represents 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 and even greater numbers of (ligand-linker-platinum compound-linker-active agent) conjugates can be contained in the nanoparticle.

In another aspect, the active agent of the conjugate comprises a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% and the platinum compound of the conjugate comprises a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% such that the sum of the molar weight percentages of the combination is 100%. For example, an active agent can comprise 40 weight percent (40% w/w), the platinum compound may comprise 30 weight percent (30% w/w) and a targeting ligand can comprise 30 weight percent (30% w/w) as contained in the nanoparticle. In another example, an active agent can comprise 50 weight percent (50% w/w), the platinum compound may comprise 20 weight percent (20% w/w) and a targeting ligand can comprise 30 weight percent (30% w/w) as contained in the nanoparticle. In yet another example, a first active agent can comprise 10 weight percent (10% w/w), a second active agent can comprise 30 weight percent (30% w/w), the platinum compound can comprise 40 weight percent (40% w/w) and a targeting ligand can comprise 20 weight percent (20% w/w) as contained in the nanoparticle. Multiple variations of such amounts are contemplated herein.

By using predetermined molar weight percentages, precise ratios between conjugated targeting ligands, platinum compounds and drugs in the nanoparticle can be provided. For example, the ligand to platinum compound to drug ratio may be about 500:1 to 1:1:1 to 1:500:1 to 1:1:500.

Also provided is a method for controlling ratios of conjugated active agent platinum compound contained in a nanoparticle inner portion, the method comprising: a) synthesizing a combination of an active agent conjugated to a linker, and a platinum compound conjugated to the same linker; b) synthesizing a combination of a targeting ligand conjugated to a linker, and conjugating this same linker to the platinum compound of step a; wherein the active agent, platinum compound and targeting ligand have a predetermined ratio; c) adding the combination to an agitated solution comprising a polar lipid; and d) adding water to the agitated solution, wherein nanoparticles are produced having a controlled ratio of conjugated active agent-ligand-platinum compound-ligand contained in the inner portion. In various aspects of the present embodiment, about 100% of the active agent, the platinum compound and the ligand contained in the inner portion are conjugated.

The present teachings also provide a combination of platinum compound and active agent having a predetermined ratio and contained in a nanoparticle inner portion. Such combinations may take various forms, e.g., two or more platinum compounds linked to the same or different active agent(s).

In another embodiment, a combination of conjugated platinum compound and active agent(s) having a predetermined ratio and contained in a nanoparticle inner portion. Such combinations may take various forms, e.g., two or more platinum compounds linked to the same or different active agent(s).

In various aspects, the solution comprising a polar lipid further comprises a functionalized polar lipid.

In another embodiment, a method is provided for producing a combination of conjugated active agents having a predetermined ratio in a nanoparticle, the nanoparticle comprising an inner portion, the method comprising: a) adding to an agitated solution comprising a polar lipid a combination of (i) a first active agent conjugated to a platinum compound by a first linker, (ii) a second active agent conjugated to the platinum compound by a second linker, (iii) a first targeting ligand conjugated to the platinum compound by a third linker, and (iv) a second targeting ligand by a fourth linker to the platinum compound, wherein the conjugates have a predetermined ratio; and b) adding water to the agitated solution, wherein nanoparticles are produced containing in the inner portion the conjugated active agents having a predetermined ratio. In various aspects, the method can further comprise isolating nanoparticles having a diameter less than about 300 nm. In various aspects, about 100% of active agents contained in the inner portion are conjugated.

Once formed, the conjugates may be formulated into nanoparticles for delivery to a patient. The compounds of the present teachings may be synthesized according to methods known in the art, including various methods described herein. The present teachings therefore comprise compositions (including pharmaceutical compositions) comprising one or more of the compounds as described herein. In various embodiments, a composition of the present teachings comprises a particle and a conjugate described herein. In some embodiments, as described further in the sections below, the particle comprises a base component forming an inner portion and an exterior portion. In certain embodiments, the interior of the particle is more hydrophobic than the exterior of the particle. In certain other embodiments, the interior is more hydrophilic than the exterior.

A. Platinum Compounds

In another embodiment, the composition of a platinum compound as described herein comprises a compound having the formula (III),

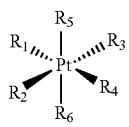

(III)

wherein $R_1$, $R_2$, $R_3$, and $R_4$ can be the same or different and each is a group comprising at least one of ammonia, an amine, a heterocycle including at least one nitrogen, an aryl group, or a leaving group, any being optionally substituted, or, any two or three of $R_1$, $R_2$, $R_3$, and $R_4$ can be joined together to form a bidentate ligand or tridentate ligand, any being optionally substituted, and $R_5$ and $R_6$ can be the same or different and comprise of the formula -$QR_7$, wherein $R_7$ is an alkyl, an alkenyl, an alkynyl, a heteroalkyl, a heteroalkenyl, a heteroalkynyl, an aryl, an oxo alkyl acid or a heteroaryl, and Q is O or N. In a particular embodiment, Q is O and $R_7$ is an oxo alkyl acid. Non-limiting examples of $R_7$ groups include $CO(CH_2)_nCOOH$ where n is 0, 1, 2, 3, 4, 5, 6, 7, 8, 9, or greater. As another non-limiting example, $R_7$ may comprise $CO(CH_2)_2COOH$.

In some cases, at least one of $R_5$ or $R_6$ may be a linker selected so as to facilitate the association of the drug precursor with the therapeutic active drug.

In some embodiments, release of $R_5$ and $R_6$ from the platinum(IV) therapeutically active precursor may form a platinum(II) therapeutically active composition. The therapeutically active platinum(II) composition may be useful for the treatment of disease, for example, cancer. In some cases, the release of $R_5$ and $R_6$ from the platinum center may be facilitated by a redox change of the platinum(IV) center. In some cases, the redox change may be caused by the release of $R_5$ and $R_6$ from the platinum(IV) center. In other cases, a redox change of the platinum(IV) center may promote the release of $R_5$ and $R_6$. For example, a redox change of the platinum(IV) center may cause a change in coordination geometry for the platinum center that reduces the number of ligands, thereby causing $R_5$ and $R_6$ to dissociate from the platinum center. As another example, the redox change of a platinum(IV) center may promote the lability of $R_5$ and $R_6$ and make it more likely that $R_5$ and $R_6$ may be replaced by other ligands.

In some embodiments, at least two of $R_1$, $R_2$, $R_3$, $R_4$, $R_5$, and $R_6$ are selected such that, upon exposure to a cellular environment, a therapeutically active platinum(II) compound forms. For example, $R_1$ and $R_2$ may be essential groups for the formation of a therapeutically active platinum agent (e.g., groups which are required for a platinum compound to be therapeutically active compound, wherein $R_3$-$R_6$ may be any variety of ligands and/or optionally absent, and at least one of $R_3$-$R_6$ is a linker). In some cases, $R_3$, $R_4$, $R_5$, and $R_6$ may be the same or different and each may be a leaving groups or a precursor to a second therapeutically active compound. In some embodiments, upon exposure to a cellular environment, $R_3$, $R_4$, $R_5$, and $R_6$ may dissociate from the platinum center, and at least two new ligands may associate with the platinum center (e.g., $R_7$ and $R_8$, as shown in Equation 1) to form a therapeutically active platinum compound (e.g., $[Pt(R_1)(R_2)(R_7)(R_8)]$).

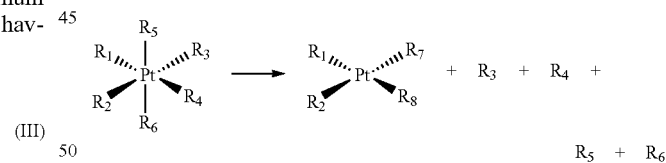

$R_7$ and $R_8$ may be the same or different and may be any suitable ligand as will be known to those of ordinary skill in the art, and are generally ligands or groups present in the environment surrounding the compound during dissociation of $R_3$, $R_4$, $R_5$ and/or $R_6$ (e.g., present in situ and/or in a cellular environment) and are capable of binding to platinum (e.g., water). It should be understood, that in some cases, less than all of $R_3$, $R_4$, $R_5$, and $R_6$ may dissociate from the platinum center and less than two ligands may associate with the platinum center. For example, $R_3$, $R_5$, and $R_6$ may dissociate from the platinum center and $R_8$ may associate, thereby forming a compound having the formula $[Pt(R_1)(R_2)(R_3)(R_8)]$. Those of ordinary skill in the art will be able to select appropriate combinations of ligands to form the desired therapeutically active complex.

In some cases, the at least two ligands are selected such that the ligands are cis to each other (e.g., $R_1$ and $R_2$, $R_1$ and $R_3$, $R_1$ and $R_5$, $R_1$ and $R_6$, $R_2$ and $R_4$, etc.). That is, the at least two ligands may not be trans to each other (e.g., $R_1$ and $R_4$, $R_2$ and $R_3$, $R_5$ and $R_6$). However, in some cases, the ligands may be selected such that they are trans to each other (e.g., in embodiments where the desired therapeutically active platinum agent has two essential ligands which are trans to each other). In some cases, the at least two ligands occupy equatorial positions of the compound. In some instances, however, one or more of the ligands may occupy an axial position of the compound. In some embodiments, more than two ligands may be essential for the formation of a therapeutically active platinum agent and those or ordinary skill in the art will be able to determine the required structure of the composition such that the essential ligands are present.

The platinum(IV) drug precursor may be more likely to undergo a redox change following uptake into a cell. That is, the reducing environment of a cell may reduce the platinum (IV) drug precursor to a platinum(II) drug. For example, a platinum(IV) drug precursor may not be reduced to form a platinum(II) drug prior to inclusion within a cell. That is, a redox change at the platinum center may precipitate release of the precursor to the second therapeutically active agent and will take advantage of the reducing environment found in cells.

In some embodiments, $R_1$, $R_2$, $R_3$, and $R_4$ may be selected such that, upon reduction of the platinum metal center and release of $R_5$ and $R_6$ (as described herein), a selected platinum(II) drug is formed. As another example, $R_1$, $R_2$, may be selected such that, upon reduction of the platinum metal center, release of $R_3$, $R_4$, $R_5$ and $R_6$, and association of $R_7$ and $R_8$ (as described herein), a selected platinum(II) drug is formed. For example, the $R_1$-$R_4$ may be selected such that the platinum(II) agent which forms comprises any known platinum(II) therapeutically active agent. Non-limiting examples of platinum(II) therapeutically active agents include cisplatin ([cis-Pt(NH$_3$)$_2$Cl$_2$]), carboplatin ([cis-Pt (NH$_3$)$_2$(1,1-(OCO)C$_4$H$_6$)]), oxaliplatin, [cis-Pt(NH$_3$)$_2$ (trans-1,2-(OCO)$_2$C$_6$H$_{10}$)], [cis-Pt(DACH)Cl$_2$] (where DACH is diaminocyclohexane), nedaplatin ([cis-Pt(NH$_3$)$_2$ OCH$_2$CHO$_2$], stratoplatin, paraplatin, platinol, cycloplatam, dexormaplatin, enloplatin, iproplatin, lobaplatin, ormaplatin, spiroplatin, zeniplatin, etc., as will be known to those of ordinary skill in the art.

In some embodiments, $R_1$-$R_4$ will generally include functional groups capable of interaction with a metal center, e.g., heteroatoms such as nitrogen, oxygen, sulfur, and phosphorus. Non-limiting examples of compounds which $R_1$-$R_4$ may comprise include amines (primary, secondary, and tertiary), aromatic amines, amino groups, amido groups, nitro groups, nitroso groups, amino alcohols, nitriles, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, $R_1$-$R_4$ may be an aryl group, alkenyl group, alkynyl group, or other moiety which may bind the metal atom in either a σ- or π-coordinated fashion. In some cases, $R_1$ and $R_2$ may be labile ligands and $R_3$ and $R_4$ may be non-labile ligands covalently bonded to the platinum metal center.

In some embodiments, any two or three of $R_1$, $R_2$, $R_3$, and $R_4$ may be joined together to form a bidentate ligand or tridentate ligand. A bidentate ligand when bound to a metal center, forms a metallacycle structure with the metal center. Bidentate ligands suitable for use in the present disclosure include species which have at least two sites capable of binding to a metal center. For example, the bidentate ligand may comprise at least two heteroatoms that coordinate the metal center, or a heteroatom and an anionic carbon atom that coordinate the metal center.

Examples of bidentate ligands suitable for use in the disclosure include, but are not limited to, alkyl and aryl derivatives of moieties such as amines, phosphines, phosphites, phosphates, imines, oximes, ethers, hybrids thereof, substituted derivatives there of, aryl groups (e.g., bis-aryl, heteroaryl-substituted aryl), heteroaryl groups, and the like. Specific examples of bidentate ligands include ethylene diamine, 2,2'-bipyridine, acetylacetonate, oxalate, and the like. Non-limiting examples of bidentate ligands include diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

In some embodiments, compounds of the disclosure may comprise a tridentate ligand, which includes species which have at least three sites capable of binding to a metal center. For example, the tridentate ligand may comprise at least three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties, triimidazoyl moieties, tris pyrazoyl moieties, and combinations of the above ligands.

The platinum compounds of the disclosure may be synthesized according to methods known in the art, including various methods described herein. For example, the method may comprise reaction of cisplatin with one or more ligand sources. In some cases, a Pt(IV) complex, wherein $R_5$ and $R_6$ are —OH, can be obtained by reaction of the parent Pt(II) species with, for example, hydrogen peroxide at temperatures ranging between about 25° C. and about 60° C. in an appropriate solvent, such as water or N,N-dimethylformamide. The desired Pt(IV) complex comprising selected $R_5$ and $R_6$ groups may be synthesized according to method known in the art, for example, by functionalization of the —OH groups (e.g., by reaction with an anhydride, an isocyanate, a pyrocarbonate, an acid chloride, etc.).

In various embodiments, $R^5$ and $R^6$ are different. For example, the compound of the present teachings can be selected from:

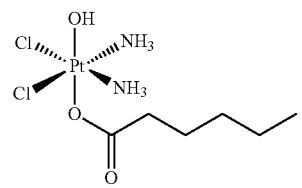

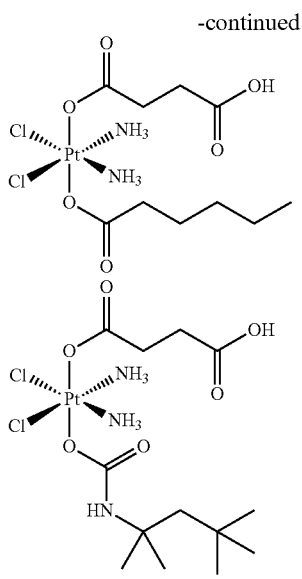

In various embodiments, $R^5$ and $R^6$ can be the same. For example, the compound of the present teachings can be selected from:

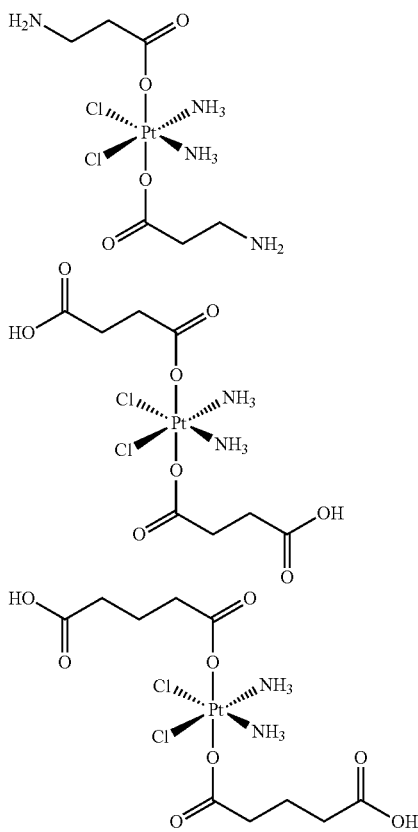

In some embodiments, a platinum complex may comprise one or more leaving groups. As used herein, a "leaving group" is given its ordinary meaning in the art and refers to an atom or a group capable of being displaced by a nucleophile. Examples of suitable leaving groups include, but are not limited to, halides (such as chloride, bromide, and iodide), alkanesulfonyloxy, arenesulfonyloxy, alkyl-carbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. A leaving group may also be a bidentate, tridentate, or other multidentate ligand. In some embodiments, the leaving group is a halide or carboxylate. In some embodiments, the leaving group is chloride.

Some embodiments of the disclosure comprise compounds having two leaving groups positioned in a cis configuration, i.e., the compound may be a cis isomer. However, it should be understood that compounds of the disclosure may also have two leaving groups positioned in a trans configuration, i.e., the compound may be a trans isomer. Those of ordinary skill in the art would understand the meaning of these terms.

Some embodiments of the disclosure provide the compound as a salt comprising a positively-charged platinum complex and a counterion (e.g., "Q"). The counterion Q may be a weak or non-nucleophilic stabilizing ion. In some cases, the counterion is a negatively-charged and/or non-coordinating ion. Examples of counterions include halides, such as chloride.

The disclosure also comprises homologs, analogs, derivatives, enantiomers, diastereomers, tautomers, cis- and trans-isomers, and functionally equivalent compositions of compounds described herein. "Functionally equivalent" generally refers to a composition capable of treatment of patients having a disease (e.g., cancer), or of patients susceptible to a disease. It will be understood that the skilled artisan will be able to manipulate the conditions in a manner to prepare such homologs, analogs, derivatives, enantiomers, diastereomers, tautomers, cis- and trans-isomers, and functionally equivalent compositions. Homologs, analogs, derivatives, enantiomers, diastereomers, tautomers, cis- and trans-isomers, and functionally equivalent compositions which are about as effective or more effective than the parent compound are also intended for use in the method of the disclosure. Such compositions may also be screened by the assays described herein for increased potency and specificity towards a disease (e.g., cancer), preferably with limited side effects. Synthesis of such compositions may be accomplished through typical chemical modification methods such as those routinely practiced in the art. Another aspect of the present disclosure provides any of the above-mentioned compounds as being useful for the treatment of a disease (e.g., cancer).

B. Linkers

In various aspects, Y is a linker bound to an active agent and the platinum complex to form a conjugate wherein the conjugate releases at least one active agent upon delivery to a target cell. In one embodiment, the linker can be a $C_1$-$C_{10}$ straight chain alkyl, $C_1$-$C_{10}$ straight chain O-alkyl, $C_1$-$C_{10}$ straight chain substituted alkyl, $C_1$-$C_{10}$ straight chain substituted O-alkyl, $C_4$-$C_{13}$ branched chain alkyl, $C_4$-$C_{13}$ branched chain O-alkyl, $C_2$-$C_{12}$ straight chain alkenyl, $C_2$-$C_{12}$ straight chain O-alkenyl, $C_3$-$C_{12}$ straight chain substituted alkenyl, $C_3$-$C_{12}$ straight chain substituted O-alkenyl, polyethylene glycol, polylactic acid, polyglycolic acid, poly(lactide-co-glycolide), polycarprolactone, polycyanoacrylate, ketone, aryl, heterocyclic, succinic ester, amino acid, aromatic group, ether, crown ether, urea, thiourea, amide, purine, pyrimidine, bypiridine, indole derivative acting as a cross linker, chelator, aldehyde, ketone, bisamine, bis alcohol, heterocyclic ring structure, azirine, disulfide, thioether, hydrazone and combinations thereof. For example, the linker can be a $C_3$ straight chain alkyl or a ketone. The present teachings also provide that the alkyl chain may optionally be interrupted by one or more atoms or groups selected from —O—, —C(=O)—, —NR, —O—C(=O)—NR—, —S—, —S—S—. The linker may be selected from dicarboxylate derivatives of succinic acid, glutaric acid or diglycolic acid.

C. Therapeutically Active Agents

A variety of therapeutic agents useful for the present teachings are known and may be identified by their effects. In some embodiments, the active agent is selected from a biomolecule, bioactive agent, small molecule, drug, prodrug, drug derivative, protein, peptide, vaccine, adjuvant, imaging agent (e.g., a fluorescent moiety) or polynucleotide.

Certain therapeutic agents are capable of preventing the establishment or growth (systemic or local) of a tumor or infection. Examples include boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals. In certain embodiments for treating or preventing the establishment or growth of a tumor, the therapeutic agent may be a small molecule, radionuclide, toxin, hormone antagonist, heavy metal complex, oligonucleotide, chemotherapeutic nucleotide, peptide, non-specific (non-antibody) protein, a boron compound or an enediyne.

In other embodiments for treating or preventing the establishment or growth of a bacterial infection, the therapeutic agent may be an antibiotic, radionuclide or oligonucleotide. In still other embodiments for treating or preventing the establishment or growth of a viral infection, the therapeutic agent may be an antiviral compound, radionuclide or oligonucleotide. In yet other embodiments for treating or preventing the establishment or growth of a fungal infection, the therapeutic agent may be an antifingal compound, radionuclide or oligonucleotide.

In some embodiments, the active agent is an anti-cancer drug such as 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cabazitaxel, cactinomycin, calcipotriol, calphostin C, calusterone, camptothecin, camptothecin derivatives, canarypox IL-2, capecitabine, caracemide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castano spermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, larotaxel, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum(IV) complexes, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxy ethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, siRNA, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spiro germanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In one embodiment, the active agent is cabazitaxel, or analogues or derivatives thereof.

In various aspects, conjugates are provided including a plurality of linkers each of which is bound to pharmaceutically active agents and platinum complex wherein the conjugate releases the pharmaceutically active agent and a platinum complex upon delivery to target cells.

Linkers can be cleaved in a variety of ways to release the active therapeutic agent and the platinum complex. These include acidic hydrolysis, enzymatic hydrolysis and reductive processes. Some chemical bonds such as hydrazone, ester and amide bonds are sensitive to acidic pH values, for example, of the intracellular environment of tumor cells. At acidic pH, hydrogen ions catalyze the hydrolysis of these bonds which in turn releases the drug from its conjugate format. In the reducing environment of the cytoplasm of tumor cells some functional groups such as Pt(IV) complexes can be reduced to active Pt(II) complexes. Therefore, both the active agent and an active form of a platinum compound can be released. Different pharmaceutically active agents, such as but not limited to cabazitaxel, platinum(IV) complexes, oxaliplatin, cisplatin, carboplatin, paclitaxel, docetaxel and the like having —OH, —NH$_2$, —SH, —COOH, alkenyl, phosphate, sulfate, heterocyclic NH, alkyne and/or ketonic groups may be covalently linked together with a suitable spacer with alkyl chains of variable lengths. These spacers may be introduced to the conjugates by reacting different acid anhydrides and any organic compounds having mono-functional or bifunctional or hetero functional groups with the active agents and targeting ligands.

The coupling reaction can be carried out under esterification conditions known to those of ordinary skill in the art such as in the presence of activating agents, e.g., carbodiimides (such as diisopropoylcarbodiimide (DIPC)), with or without catalyst such as dimethylaminopyridine (DMPA). This reaction can be carried our in an appropriate solvent, such as dichloromethane, chloroform or ethyl acetate, at a temperature or between about 0° C. and the reflux temperature of the solvent (e.g., ambient temperature).

In other aspects, where the linker is a disuccinate group, the precursor employed is succinic anhydride.

The coupling reaction is generally performed in a solvent such as pyridine or in a chlorinated solvent in the presence of a catalyst such as DMAP or pyridine at a temperature between about 0° C. and the reflux temperature of the solvent (e.g., ambient temperature).

In one embodiment, the coupling reagent is selected from the group consisting of 4-(2-pyridyldithio)-butanoic acid, and a carbodiimide copling reagent such as DCC in a chlorinated, ethereal or amidic solvent (such as N,N-dimethylformamide) in the presence of a catalyst such as DMAP at a temperature between about 0° C. and the reflux temperature of the solvent (e.g., ambient temperature).

In certain embodiments, the active agent(s) of the conjugate comprises a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% such that the sum of the molar weight percentages of the components of the conjugate is 100%. The amount of active agent(s) of the conjugate may also be expressed in terms of proportion to the platinum compound. For example, the present teachings provide a ratio of active agent to platinum compound of about 10:1, 9:1, 8:1, 7:1, 6:1, 5:1, 4:1, 3:1, 2:1, 1:1, 1:2, 1:3, 1:4; 1:5, 1:6, 1:7, 1:8, 1:9, or 1:10.

D. Targeting Ligands

Targeting ligands or moieties useful according to the present teachings include a peptide, antibody mimetic, nucleic acid (e.g. aptamer), polypeptide (e.g. antibody), glycoprotein, small molecule, carbohydrate, or lipid. In one embodiment, X can be a peptide such as somatostatin, octeotide, EGF or RGD-containing peptides, nucleic acid (e.g. aptamer), polypeptide (e.g. antibody or its fragment), glycoprotein, small molecule, carbohydrate, or lipid. In another embodiment, X can be a an aptamer being either RNA or DNA or an artificial nucleic acid; small molecules; carbohydrates such as mannose, galactose and arabinose; vitamins such as ascorbic acid, niacin, pantothenic acid, carnitine, inositol, pyridoxal, lipoic acid, folic acid (folate), riboflavin, biotin, vitamin $B_{12}$, vitamin A, E, and K; a protein such as thrombospondin, tumor necrosis factors (TNF), annexin V, interferons, angiostatin, endostatin, cytokines, transferrin, GM-CSF (granulocyte-macrophage colony-stimulating factor), or growth factors such as vascular endothelial growth factor (VEGF), hepatocyte growth factor (HGF), platelet-derived growth factor (PDGF), basic fibroblast growth factor (bFGF), and epidermal growth factor (EGF).

In another embodiment, the targeting ligand comprises an antibody mimetic selected from the group consisting of an Adnectin, Affibody, Affilin, Affitin, Anticalin, Avimer (avidity multimer), DARPin, Fynomer, Kunitz domain peptide, and Monobodies. In certain cases, such mimetics are artificial peptides or proteins with a molar mass of about 3 to 20 kDa. Nucleic acids and small molecules are sometimes considered antibody mimetics as well and are contemplated herein.

In one embodiment, the targeting ligand is arginylglycylaspartic acid (RGD peptide). It is a tripeptide composed of L-arginine, glycine, and L-aspartic acid. The sequence is a common element in cellular recognition. Arginylglycylaspartic acid is used as a biochemical tool in the study of this recognition. More specifically, it displays a strong affinity and selectivity to the alpha-V-beta-3 integrin found in tumor cells.

In another example, a targeting moiety can be an aptamer, which is generally an oligonucleotide (e.g., DNA, RNA, or an analog or derivative thereof) that binds to a particular target, such as a polypeptide. In some embodiments, the targeting moiety is a polypeptide (e.g. an antibody that specifically recognizes a tumor marker). In certain embodiments, the targeting moiety is an antibody or a fragment thereof. In certain embodiments, the targeting moiety is an Fc fragment of an antibody.

In some embodiments, a target may be a marker that is exclusively or primarily associated with a target cell, or one or more tissue types, with one or more cell types, with one or more diseases, and/or with one or more developmental stages. In some embodiments, a target can comprise a protein (e.g. cell surface receptor, transmembrane protein, glycoprotein, etc.), a carbohydrate (e.g. glycan moiety, glycocalyx, etc.), a lipid (e.g. steroid, phospholipid, etc.), and/or a nucleic acid (e.g. DNA, RNA, etc.).

In yet other embodiments, X is a ligand described in the Therapeutic Target Database, see, e.g., Zhu et al., Update of TTD: Therapeutic Target Database, Nucleic Acids Res. 38 (1): 787-91 (2010), or a ligand that targets one or more of the proteins, nucleic acids, diseases or pathways described therein. Such ligands and targets are incorporated herein by reference. Additionally useful for the present teachings herein, Applicant further incorporates herein by reference the ligands and targets from the following United States Patents and United States Applications: U.S. Pat. Nos. 7,501,120; 8,105,568; 8,012,485; 7,964,567; 7,498,025; 8,039,273; 7,601,332; 7,659,241; 20120329071; 20120329886; 20120329065; 20120328604; 20120322672; 20120309691; 20120308569; 20120329870; 20120329672; 20110275558; 20090280056; 20120253021; 20080171040; 20080305044; 20100324008; 20110085974; 20120065149.

In some embodiments, the target, target cell or marker is a molecule that is present exclusively or in higher amounts on a malignant cell, e.g., a tumor antigen. In some embodiments, a marker is a prostate cancer marker. In certain embodiments, the prostate cancer marker is prostate specific membrane antigen (PSMA), a 100 kDa transmembrane glycoprotein that is expressed in most prostatic tissues, but is more highly expressed in prostatic cancer tissue than in normal tissue. PSMA is a reported tumor marker that is up-regulated in prostate cancer, particularly in advanced, hormone-independent, and metastatic disease (Ghosh and Heston, 2004, J. Cell. Biochem., 91:528-539). PSMA has been employed as a tumor marker for imaging of metastatic prostate cancer and as a target for experimental immunotherapeutic agents. PSMA is the molecular target of ProstaScint®, a monoclonal antibody-based imaging agent approved for diagnostic imaging of prostate cancer metastases. Interestingly, PSMA is differentially expressed at high levels on the neovasculature of most non-prostate solid tumors, including breast and lung cancers, and the clinical feasibility of PSMA targeting for non-prostate cancers was demonstrated in two distinct clinical trials (Morris et al., 2007, Clin. Cancer Res., 13:2707-13; Milowsky et al, 2007, J. Clin. Oncol, 25:540-547). Therefore, the highly restricted presence of PSMA on prostate cancer cells and non-prostate solid tumor neovasculature makes it an attractive target for delivery of cytotoxic agents to most solid tumors.

In other embodiments, a marker is a breast cancer marker, or a colon cancer marker, or a rectal cancer marker, or a lung cancer marker, or a pancreatic cancer marker, or a ovarian cancer marker, or a bone cancer marker, or a renal cancer marker, or a liver cancer marker, or a neurological cancer marker, or a gastric cancer marker, or a testicular cancer marker, or a head and neck cancer marker, or a esophageal cancer marker, or a cervical cancer marker.

Several other cell surface markers are useful herein as potential targets for tumor-homing therapeutics, including, for example HER-2, HER-3, EGFR, and the folate receptor.

In other embodiments, the targeting ligand binds a target selected from the group consisting of CD19, CD70, CD56, PSMA, Alpha integrin, CD22, CD138, EphA2, AGS-5, Nectin-4, HER2, GPMNB, CD74 and Le.

In certain embodiments, the targeting ligand(s) of the conjugate comprises a predetermined molar weight percentage from about 1% to 10%, or about 10% to about 20%, or about 20% to about 30%, or about 30% to 40%, or about 40% to 50%, or about 50% to 60%, or about 60% to 70%, or about 70% to 80%, or about 80% to 90%, or about 90% to 99% such that the sum of the molar weight percentages of the components of the conjugate is 100%. The amount of targeting ligand(s) of the conjugate may also be expressed in terms of proportion to the platinum compound. For example, the present teachings provide a ratio of ligand to platinum compound of about 10:1, 9:1, 8:1, 7:1, 6:1, 5:1, 4:1, 3:1, 2:1, 1:1, 1:2, 1:3, 1:4; 1:5, 1:6, 1:7, 1:8, 1:9, or 1:10.

In a further embodiment, the nanoparticles may contain a plurality of the same Pt-Y-Z conjugates, or may optionally contain a plurality of conjugates wherein Pt-Y-Z are different.

In one embodiment, a cabazitaxel-platinum(IV) monohexanoate-monosuccinate conjugate of Formula II is provided as follows.

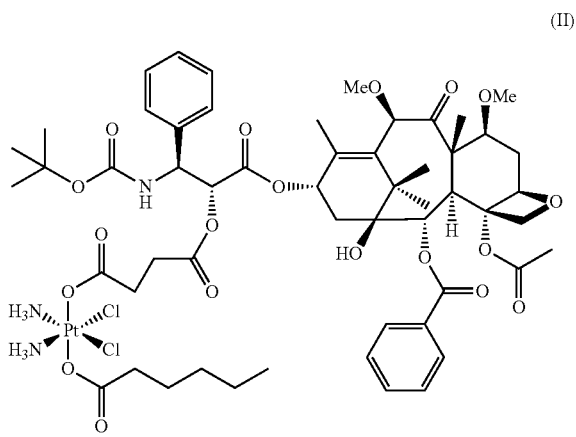

(II)

III. Formulation of Nanoparticles

The conjugate taught herein may be formulated as nanoparticles. In some embodiments it is encapsulated, in whole or in part, in the inner portion of the nanoparticles. The nanoparticles may have a substantially spherical or non-spherical configuration (e.g., upon swelling or shrinkage). The nanoparticles may include polymer blends. In various embodiments, the base component of the nanoparticles comprises a polymer, a small molecule, or a mixture thereof. The base component can be biologically derived. For example, the small molecule can be, for example, a lipid. A "lipid," as used herein, refers to a hydrophobic or amphiphilic small molecule. Without attempting to limit the scope of the present teachings, lipids, because of their amphiphilicity, can form particles, including liposomes and micelles.

In some embodiments, the base component comprises a polymer. For example, the polymer can be a biopolymer. Non-limiting examples include peptides or proteins (i.e., polymers of various amino acids), nucleic acids such as DNA or RNA. In certain embodiments, the polymer is amphiphilic, i.e., having a hydrophilic portion and a hydrophobic portion, or a relatively hydrophilic portion and a relatively hydrophobic portion.

In various embodiments, the base component is biocompatible, i.e., it does not typically induce an adverse response when inserted or injected into a subject. The adverse response can include significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject.

Non-limiting examples of biocompatible polymers that may be useful in various embodiments of the present disclosure include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

In various embodiments, the base component is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) can be days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Examples of biodegradable polymers include, but are not limited to, poly(lactide) (or poly(lactic acid)), poly(glycolide) (or poly(glycolic acid)), poly(ortho esters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In various embodiments, the base component comprises polylactide or poly(lactic acid). In various embodiments, the base component comprises poly(glycolide). In various embodiments, the base component comprises poly(lactide-co-glycolide).

A person with ordinary skill in the art can choose polylactide, polyglycolide, or poly(lactide-co-glycolide) of different molecular weights according to various applications. In some embodiments, the polylactide, polyglycolide, or poly(lactide-co-glycolide) has a number average molecular weight of about 5 kDa to about 250 kDa. For example, the polylactide, polyglycolide, or poly(lactide-co-glycolide) has a number average molecular weight of about 5 kDa to about 150 kDa. In certain embodiments, the polylactide, polyglycolide, or poly(lactide-co-glycolide) has a number average molecular weight of about 5 kDa to about 10 kDa, about 10 kDa to about 20 kDa, about 20 kDa to about 30 kDa, about 30 kDa to about 40 kDa, about 40 kDa to about 50 kDa, about 50 kDa to about 60 kDa, about 60 kDa to about 70 kDa, about 70 kDa to about 80 kDa, about 80 kDa to about 90 kDa, about 90 kDa to about 100 kDa, about 100 kDa to about 110 kDa, about 110 kDa to about 120 kDa, about 120 kDa to about 130 kDa, about 130 kDa to about 140 kDa, or about 140 kDa to about 150 kDa. In certain embodiments, the polylactide, polyglycolide, or poly(lactide-co-glycolide) has a number average molecular weight of about 10 kDa to about 150 kDa, about 20 kDa to about 125 kDa, about 30 kDa to about 110 kDa, about 40 kDa to about 90 kDa, or about 50 kDa to about 80 kDa. For example, the polylactide, polyglycolide, or poly(lactide-co-glycolide) can have a number average molecular weight of about 15 kDa, about 35 kDa, about 50 kDa, about 60 kDa, about 80 kDa, about 90 kDa, about 100 kDa, or about 110 kDa. In particular embodiments, the polylactide, polyglycolide, or poly(lactide-co-glycolide) has a number average molecular weight of about 15 kDa.

In various embodiments, the base component has the capability of controlling immunogenicity. Nonexclusive examples of a polymeric base component include a poly(alkylene glycol) (also known as poly(alkylene oxide)), such as poly(propylene glycol), or poly(ethylene oxide), also known as poly(ethylene glycol) ("PEG"), having the formula —(CH$_2$—CH$_2$—O)$_n$—, where n is any positive integer. The poly(ethylene glycol) units may be present within the polymeric base component in any suitable form. For instance, the polymeric base component may be a block copolymer where one of the blocks is poly(ethylene glycol). A polymer comprising poly(ethylene glycol) repeating units is also referred to as a "PEGylated" polymer. Such polymers can control inflammation and/or immunogenicity (i.e., the ability to provoke an immune response), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. For example, PEGylation may be used to create particles which comprise an interior which is more hydrophobic than the exterior of the particles. In some cases, the addition of poly(ethylene glycol) repeating units may increase plasma half-life of the polymeric conjugate, for instance, by decreasing the uptake of the polymer by the phagocytic system while decreasing transfection/uptake efficiency by cells.

In various embodiments, the PEG unit has a number average molecular weight of about 1 kDa to about 20 kDa. For example, the PEG unit can have a number average molecular weight of about 1 kDa to about 2 kDa, about 2 kDa to about 3 kDa, about 3 kDa to about 4 kDa, about 4 kDa to about 5 kDa, about 5 kDa to about 6 kDa, about 6 kDa to about 7 kDa, about 7 kDa to about 8 kDa, about 8 kDa to about 9 kDa, about 9 kDa to about 10 kDa, about 10 kDa to about 12 kDa, about 12 kDa to about 14 kDa, about 14 kDa to about 16 kDa, about 16 kDa to about 18 kDa, or about 18 kDa to about 20 kDa. In some embodiments, the PEG unit has a number average molecular weight of about 1 kDa to about 10 kDa. In certain embodiments, the PEG unit has a number average molecular weight of about 2 kDa to about 8 kDa, or about 3 kDa to about 7 kDa, or about 4 kDa to about 6 kDa. For example, the PEG unit has a number average molecular weight of about 2 kDa to about 6 kDa or about 3 kDa to about 5 kDa. In particular embodiments, the PEG unit has a number average molecular weight of about 3 KDa, 4 kDa, 5 kDa, or 6 kDa.

In various embodiments, the basis component comprises a polylactide, a polyglycolide, or poly(lactide-co-glycolide) and a PEGylated polylactide, a PEGylated polyglycolide, or a PEGylated poly(lactide-co-glycolide). The weight percentage of the PEGylated polymer in the base component can be from 0% to 100%, including about 5% to about 95%, about 10% to about 90%, about 20% to about 80%, about 30% to about 70%, or about 40% to about 60%. In some embodiments, the weight percentage of the PEGylated polymer in the base component is about 30% to about 95% or about 40% to about 90%. In particular embodiments, the weight percentage of the PEGylated polymer in the base component is about 40%, 50%, 60%, 70%, 80%, 90%, or 100%. For example, the weight percentage of the PEGylated polymer in the base component is about 60%.

Those of ordinary skill in the art will know of methods and techniques for PEGylating a polymer, for example, by using EDC (1-ethyl-3-(3-dimethylaminopropyl)carbodiimide hydrochloride) and NHS (N-hydroxysuccinimide) to react a polymer to a PEG group terminating in an amine, for example, by ring opening polymerization techniques, or the like. In addition, certain embodiments of the disclosure are directed towards copolymers containing poly(ester-ether)s, e.g., polymers having repeating units joined by ester bonds (e.g., R—C(O)—O—R' bonds) and ether bonds (e.g., R—O—R' bonds).

In various embodiments, the particle comprises one or more compounds of the present teachings. In some embodiments, at least one of the compounds is contained within a particle of the present teachings. The term "contained within" may mean "located in a cavity of," "entirely embedded in," or "partially embedded in." For example, at least one of the compounds can be located in a cavity formed in a particle of the present teachings or otherwise embedded in a particle of the present teachings. In certain embodiments, at least one of the compounds is located in the cavity of a particle. In certain embodiments, at least one of the compounds is entirely embedded in a particle. In certain embodiments, at least one of the compounds is partially embedded in a particle.

In various embodiments, a substantial amount of at least one of the compounds is contained within particles of the present teachings. In some embodiments, about 90% or greater, about 80% or greater, about 70% or greater, or about 60% or greater of the total amount of at least one of the compounds included in the particles is contained within the particles. In certain embodiments, about 80% or greater of the total amount of at least one of the compounds included in the particles is contained within the particles. In certain embodiments, about 90% or greater of the total amount of at least one of the compounds included in the particles is contained within the particles. In certain embodiments, about 95% or greater of the total amount of at least one of the compounds included in the particles is contained within the particles.

In various embodiments, about 50% and greater, about 40% or greater, about 30% or greater, about 20% or greater, or about 10% or greater of the total amount of at least one of the compounds included in particles of the present teachings is contained within the particles. In some embodiments, about 10% or greater of the total amount of at least one of the compounds included in the particles is contained within the particles. In some embodiments, about 20% or greater of the total amount of at least one of the compounds included in the particles is contained within the particles. In some embodiments, about 30% or greater of the total amount of at least one of the compounds included in the particles is contained within the particles. In some embodiments, about 40% or greater of the total amount of at least one of the compounds included in the particles is contained within the particles. In some embodiments, about 50% or greater of the total amount of at least one of the compounds included in the particles is contained within the particles.

In various embodiments, the ratio of the compound to the base component in a solution prior to formation of a plurality of particles may affect the percent loading of the compound in the particle and/or the mean size of the particle. For example, an increase in the percent weight of the compound to the percent weight of the base component may increase the percent loading of the compound within the particle. However, the percent loading of the compound in the particles formed may or may not be related to the weight percent of the compound provided during formation of the particles.

In some embodiments, the percent weight of the compound provided in a mixture comprising the compound and the base component is at least about 5%, at least about 10%, at least about 20%, at least about 30%, at least about 40%, at least about 50%, at least about 60%, at least about 70%, at least about 80%, at least about 90%, at least about 100%, or greater. In certain embodiments, the percent weight is between about 5% and about 90%, between about 10% and about 80%, between about 10% and about 50%, between about 50% and about 90%, or any range therein. In particular embodiments, the weight percentage is about 5% to about 30% or about 5% to about 20%. For example, the weight percentage can be about 10%.

In some embodiments, the total percent loading of the compound in the plurality of particles is greater than about 0.01%, greater than about 0.05%, greater than about 0.1%, greater than about 0.5%, greater than about 1%, greater than about 2%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, or greater. In some embodiments, the percent loading is between about 0.01% and about 50%, between about 0.05% and about 30%, between about 0.1% and about 10%, between about 1% and about 10%, between about 0.05% and about 30%, between about 0.05% and about 10%, between about 0.1% and about 50%, or any range therein. In certain embodiments, the percentage loading is about 2%, about 3%, about 4%, about 5%, about 6%, about 7%, or about 8%. In particular embodiments, the percentage loading is about 5%, about 6%, about 7%, about 8%, about 9%, or about 10%.

Without wishing to be bound by theory, the size of a particle may alter the delivery (e.g., loss of payload, drug efflux, aggregations, delivery to desired location, etc.) of a compound of the present teachings from the particles. The size of the particles used in a delivery system may be selected based on the application, and will be readily known to those of ordinary skill in the art. For example, particles of smaller size (e.g., <200 nm) may be selected if systematic delivery of the particles throughout a patient's bloodstream is desired. As another example, particles of larger size (e.g., >200 nm) may be selected if sequestering of the particles by a patient's reticuloendothelial system upon injection is desired (e.g., sequestering of the particles in the liver, spleen, etc.). The desired length of time of delivery may also be considered when selecting particle size. For example, smaller particles may circulate in the blood stream for longer periods of time than larger particles.

In some embodiments, the particles may substantially accumulate at the site of a tumor. Without attempting to limit the scope of the present teaching, the accumulation may be due, at least in part, to the presence of a targeting moiety associated with the particle, as described herein; or, at least in part, due to an enhanced permeability and retention (EPR) effect, which allows for particles to accumulate specifically at a tumor site. The EPR effect will be known to those of ordinary skill in the art and refers to the property by which certain sizes of material (e.g., particles) tend to accumulate in tumor tissue much more than they do in normal tissues.

In various embodiments, a particle may be a nanoparticle, i.e., the particle has a characteristic dimension of less than about 1 micrometer, where the characteristic dimension of a particle is the diameter of a perfect sphere having the same volume as the particle. The plurality of particles can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 50 nm, at least about 100 nm, at least about 150 nm, or greater. In certain embodiments, the plurality of the particles have an average diameter of about 10 nm, about 25 nm, about 50 nm, about 100 nm, about 150 nm, about 200 nm, about 250 nm, about 300 nm, about 500 nm, or the like. In some embodiments, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles have an average diameter between about 10 nm and about 500 nm, between about 20 nm and about 400 nm, between about 30 nm and about 300 nm, between about 40 nm and about 200 nm, between about 50 nm and about 175 nm, between about 60 nm and about 150 nm, between about 70 nm and about 120 nm, or the like. For example, the average diameter can be between about 70 nm and 120 nm.

Another aspect of the present teachings relates to systems and methods of making the disclosed particles, including nanoparticles. In various embodiments, a method of making the particles comprises providing a compound disclosed herein; providing a base component (e.g., PLA-PEG or PLGA-PEG); combining the compound and the base component in an organic solution to form a first organic phase; and combining the first organic phase with a first aqueous solution to form a second phase; emulsifying the second phase to form an emulsion phase; and recovering particles. In various embodiments, the emulsion phase is further homogenized.

In some embodiments, the first phase includes about 5 to about 50% weight, e.g. about 1 to about 40% solids, or about 5 to about 30% solids, e.g. about 5%, 10%, 15%, and 20%, of the compound and the base component. In certain embodiments, the first phase includes about 5% weight of the compound and the base component. In various embodiments, the organic phase comprises acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or a combination thereof. In some embodiments, the organic phase includes benzyl alcohol, ethyl acetate, or a combination thereof In various embodiments, the aqueous solution comprises a water, sodium cholate, ethyl acetate, or benzyl alcohol. In some embodiments, the aqueous solution also comprises an emulsifier, including a polysorbate. For example, the aqueous solution can include polysorbate 80.

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g. probe sonicator or a high pressure homogenizer, e.g. by using 1, 2, 3 or more passes through a homogenizer. For example, when a high pressure homogenizer is used, the pressure used may be about 4000 to about 8000 psi, or about 4000 to about 5000 psi, e.g. 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g. about 0 to about 10° C., or about 0 to about 5° C.).

In various embodiments, the particles are recovered by filtration. For example, ultrafiltration membranes can be used. Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (5-25 nm) may be used.

In various embodiments, a compound of the present teachings contained within a particle is released in a controlled manner. The release can be in vitro or in vivo. For example, particles of the present teachings can be subject to a release test under certain conditions, including those specified in the U.S. Pharmacopeia and variations thereof.

In various embodiments, less than about 90%, less than about 80%, less than about 70%, less than about 60%, less than about 50%, less than about 40%, less than about 30%, less than about 20% of the compound of the present teachings contained within particles is released in the first hour after the particles are exposed to the conditions of a release test. In some embodiments, less that about 90%, less than about 80%, less than about 70%, less than about 60%, less than about 50% of the compound of the present teachings contained within particles is released in the first hour after the particles are exposed to the conditions of a release test. In certain embodiments, less than about 50% of the compound contained within particles is released in the first hour after the particles are exposed to the conditions of a release test.

With respect to a compound of the present teachings being released in vivo, for instance, the compound contained within a particle administered to a subject may be protected from a subject's body, and the body may also be isolated from the compound until the compound is released from the particle.

Thus, in some embodiments, the compound may be substantially contained within the particle until the particle is delivered into the body of a subject. For example, less than about 90%, less than about 80%, less than about 70%, less than about 60%, less than about 50%, less than about 40%, less than about 30%, less than about 20%, less than about 15%, less than about 10%, less than about 5%, or less than about 1% of the total compound is released from the particle prior to the particle is delivered into the body, for example, a treatment site, of a subject. In some embodiments, the compound may be released over an extended period of time or by bursts (e.g., amounts of the compound are released in a short period of time, followed by a periods of time where substantially no compound is released). For example, the compound can be released over 6 hours, 12 hours, 24 hours, or 48 hours. In certain embodiments, the compound is released over 1 week or 1 month.

In further embodiments, the particle is a microparticle, nanoparticle or picoparticle. In still other embodiments, the particle is a liposome, polymeric micelle, lipoplex or polyplex. In some embodiments, the particle comprises one or more lipids. In some embodiments, the one or more lipids are lipidoids. In other embodiments, the particle further comprises one or more polymers. In still other embodiments, one or more of the lipids are conjugated to one or more of the polymers. In some embodiments, the particle comprises one or more polymers. In some embodiments, one or more of the lipids or polymers are degradable.

In some embodiments, the particle has an average characteristic dimension of less than about 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm or 20 nm. In other embodiments, the particle has an average characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm. In further embodiments, the particle has an average characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

In various embodiments, the base component is biocompatible, i.e., it does not typically induce an adverse response when inserted or injected into a subject. The adverse response can include significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject.

Non-limiting examples of biocompatible polymers that may be useful in various embodiments of the present disclosure include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

In various embodiments, the base component is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Other embodiments, objects, features, and advantages will be set forth in the detailed description of the embodiments that follow and, in part, will be apparent from the description or may be learned by practice of the claimed disclosure. These objects and advantages will be realized and attained by the compositions and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

The compound may thus be contained, in large part or essentially completely within the interior of the particle, which may thus shelter it from the external environment surrounding the particle (or vice versa). For instance, a compound of the present teachings contained within a particle administered to a subject may be protected from a subject's body, and the body may also be isolated from the compound until the compound is released from the particle.

IV. Pharmaceutical Preparations

In another embodiment, a pharmaceutical composition is provided comprising the conjugate above, or a pharmaceutically acceptable salt thereof, in a pharmaceutically acceptable vehicle. The amount of a conjugate that may be combined with a pharmaceutically acceptable carrier to produce a dosage form will vary depending upon the host treated. The nanoparticulate conjugate may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the compositions taught herein may be formulated in powder form for constitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 5 percent to about 20 percent, for example, from about 5 percent to about 17 percent, from about 8 to about 14 percent, or from about 10 percent of the compound.

V. Methods of Treating Diseases and Conditions

In additional aspects, the disclosure features methods of treating a disorder, e.g., a cancer or other disorder disclosed herein, in a subject in need thereof, the method comprising administering to the subject a therapeutically effective amount of a composition (e.g., composition comprising an active agent linked to a platinum compound) or as a particle described above. In some embodiments, the active agent isselected to treat the disorder.

In some embodiments, the particle, e.g., nanoparticle, described herein may substantially accumulate at the site of a tumor (e.g., the accumulation of a component of an active agent-linker-platinum compound composition associated with a nanoparticle, after administration to a subject that has a tumor, is present at a tumor site in a higher concentration than a component of the active agent-linker-platinum-composition that is not associated with a nanoparticle. Without attempting to limit the scope of the present teaching, the accumulation may be due, at least in part, the presence of a targeting moiety associated with the particle, as described herein; or, at least in part, due to an enhanced permeability and retention (EPR) effect, which allows for particles to accumulate specifically at a tumor site. The EPR effect is known to those of ordinary skill in the art and refers the property by which certain sizes of material (e.g., particles) tend to accumulate in tumor tissue much more than they do in normal tissues.

In some aspects, the teachings herein feature methods of delivering the nanoparticles to a biological target within a subject. The methods can include obtaining a pharmaceutical composition comprising a plurality of particles disclosed herein that include a targeting agent, wherein the targeting agent binds specifically to the biological target; and administering to the subject the pharmaceutical composition in an amount effective to deliver the active agents in the particles to the biological target. In some embodiments, the targeting agent specifically binds to a tumor cell or tumor vasculature.

The pharmaceutical composition may comprise a plurality of particles disclosed herein that include a platinum complex and an active agent encapsulated in a nanoparticle.

These and other embodiments of the present teachings may also involve promotion of the treatment of cancer or tumor according to any of the techniques and compositions and combinations of compositions described herein.

In various embodiments, methods for treating a subject having a cancer are provided, wherein the method comprises administering a therapeutically-effective amount of a compound, as described herein, to a subject having a cancer or suspected of having cancer. In some embodiments, the subject may be otherwise free of indications for treatment with said compound. In some embodiments, methods include use of cancer cells, including but not limited to mammalian cancer cells. In some instances, the mammalian cancer cells are human cancer cells.

In some embodiments, the compounds of the present teachings have been found to inhibit cancer growth, including proliferation, invasiveness, and metastasis, thereby rendering them particularly desirable for the treatment of cancer.

In some embodiments, the compounds of the present teachings may be used to prevent or inhibit the growth of a tumor or cancer, and/or to prevent the metastasis of a tumor or cancer. In some embodiments, compositions of the present teachings may be used to shrink or destroy a cancer.

The cancers treatable by methods of the present teachings generally occur in mammals. Mammals include, for example, humans and other primates, as well as pet or companion animals, such as dogs and cats, laboratory animals, such as rats, mice and rabbits, and farm animals, such as horses, pigs, sheep, and cattle. In various embodiments, the cancer is lung cancer, breast cancer, colorectal cancer, ovarian cancer, bladder cancer, prostate cancer, cervical cancer, renal cancer, leukemia, central nerve system cancers, myeloma, and melanoma. In some embodiments, the cancer is lung cancer. In certain embodiments, the cancer is human lung carcinoma and/or normal lung fibroblast.

In certain embodiments, a cabazitaxel-platinum (IV) composition or nanoparticle of the present disclosure, or pharmaceutically acceptable counter ions or salts thereof, are administered in a therapeutically effective amount based on calculation of the body surface area (BSA). Such amount ranges from about 10 m g/m$^2$ BSA to about 50 mg/m$^2$ administered IV wherein the mg corresponds to the total amount of cabazitaxel delivered per dose. In one embodiment, the therapeutically effective amount is 25 mg/m$^2$ BSA administered as a one-hour IV infusion.

VI. Examples

The following examples are intended to illustrate certain embodiments of the present teachings, but do not exemplify the full scope of the present teachings and therefore should not be construed to limit the scope of the present teachings.

EXAMPLE 1

Synthesis of Cabazitaxel-Platinum(IV) Monohexanoate-Monosuccinate Conjugate (II)

Platinum (IV) diamminedichlorohexanoate-succinate (compound 1) Reaction Scheme:

Method:

Platinum (IV) diamminedichlorosuccinate (983 mg, 2.26 mmol) was dissolved in N,N-dimethylformamide (29 mL) and hexanoic anhydride (576 mL, 2.42 mmol) was added. The reaction was stirred for 16 hours at ambient temperature. The solvent was removed under vacuum at 38° C. and the residue was co-evaporated with methanol (3×10 mL) to remove residual DMF. The residue was dissolved in methanol (2 mL) and the solution was added to tert-butylmethylether (25 mL) to give a white precipitate. The solution was spun-down using a centrifuge (500 rpm, 5° C.) and the supernatant decanted. The solid plug was resuspended in tert-butylmethylether (20 mL) and spun-down again. The supernatant was removed and the plug suspended in tert-butylmethylether (20 mL). The suspension was filtered to give a white solid that was dried under high vacuum at 40° C., to yield 800 mg of product (1.5 mmol, 67% yield). The product was analyzed by HPLC (method 2) and gave a peak retention time of 1.4 minutes versus the starting material retention time of 2.8 minutes. Analysis by LCMS (Waters ZQ Micromass) gave a peak at 532 (MH$^+$). Characterization by 1HNMR (Varian 400 MHz) d6-DMSO gave δ 6.5 (6H, b), δ 2.5 (2H, m), δ 2.2 (2H, t), δ 1.4 (2H, m), δ 1.2 (4H, m), δ 0.8 (3H, t).

HPLC Method 2 (HILIC)
Column: Hypersil GOLD HILIC 4.6×100 mm, 3 micron, Thermo Scientific PN: 26503-104630
Mobile phase: A=DMF, B=Methanol, C=100 mM Ammonium formate, pH 3.5.
Flow: 1.5 mL/min
Column Temp: 40° C.
Detection: UV 310 and 270 nm
Injection Volume: 5 uL of a 1 mg/mL sample in DMSO
Gradient:

| Time (mins) | % A | % B | % C |
|---|---|---|---|
| 0 | 30 | 50 | 20 |
| 8 | 55 | 5 | 40 |

Cabazitaxel-platinum(IV)-diammine dichlorohexanoate-succinate Reaction Scheme:

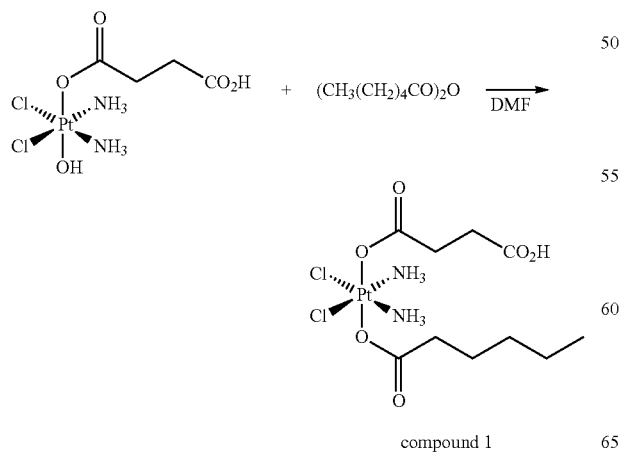

compound 1

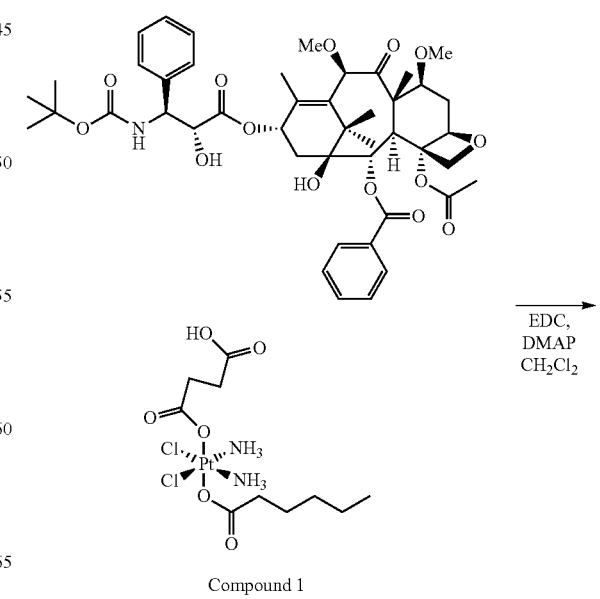

Compound 1

-continued

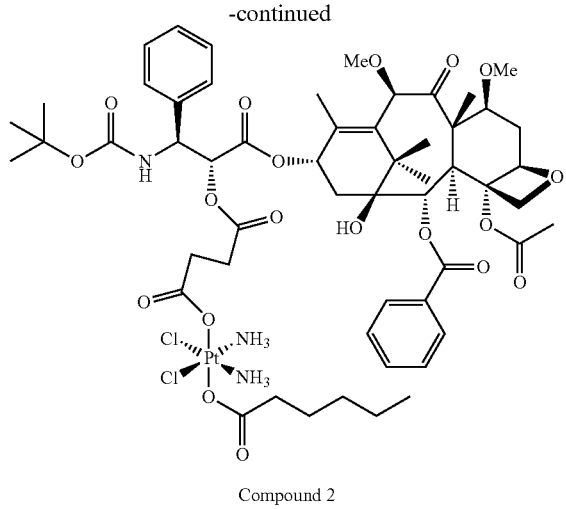

Compound 2

Method:

Platinum (IV) diamminedichlorohexanoate-succinate (compound 1, 100 mg, 0.19 mmol) was dissolved in methylene chloride (5 mL) and 4-dimethylaminopyridine (23 mg, 0.19 mmol) and 1-ethyl-3-[3-dimethylaminopropyl]carbodiimide hydrochloride (36 mg, 0.19 mmol) were added. To the stirred reaction mixture was added cabazitaxel (157 mg, 0.18 mmol). The reaction was stirred for 16 hours under a nitrogen atmosphere. To the reaction was added methylene chloride (30 mL) and the organics were washed twice with hydrochloric acid (0.1 M, 10 mL) and once with water (10 mL). The organic layer was then dried over sodium sulfate. After filtration the organic filtrate was concentrated under vacuum and the resulting oil was dried under high vacuum at ambient temperature to give a yellow foam (compound XX, 240 mg, 0.17 mmol, 94% yield). The product was analyzed by LCMS (Method 1) and gave a new peak retention time 6.29 minutes (cabazitaxel has a retention time of 6.07 minutes). The new peak Rt-6.29 gave the product parent ion of 1352 ($MH^+$) when analyzed by mass spectroscopy (Water ZQ Micromass).

HPLC Method 1: C18 Reverse Phase Method
Column: Zorbax Eclipse XDB-C18 4.6×100 mm, 3.5 micron, Agilent PN: 961967-902.
Mobile phase: A=Water+0.1% TFA B=Acetonitrile+0.1% TFA
Flow: 1.5 mL/min
Column Temp: 35° C.
Detection: UV 310 and 254 nm
Injection Volume: 10 uL
Gradient:

| Time (mins) | % A | % B |
|---|---|---|
| 0 | 95 | 5 |
| 6 | 5 | 95 |
| 8 | 5 | 95 |
| 8.01 | 95 | 5 |
| 10 | 95 | 5 |

EXAMPLE 2

Nanoparticles of the Cabazitaxel-Platinum(IV) Monohexanoate-Monosuccinate Conjugate (II)

Cabazitaxel-platinum(IV) monohexanoate-monosuccinate nanoparticles of formula (II) were prepared using oil/water emulsion, high-pressure homogenization, and tangential flow filtration. 40/60% w/w $PLA_{108}/PLA_{35}$ $mPEG_5$ were dissolved in ethyl acetate to achieve a concentration of 50 mg/mL and cabazitaxel-platinum(IV) monohexanoate-monosuccinate (II) added to achieve a 10% w/w drug conjugate content relative to the polymer. The oil phase was then slowly added to the aqueous phase containing 0.2% w/v polysorbate 80 (10/90% v/v oil/water) and a course emulsion formed using a rotor-stator. The course emulsion was then processed through a high-pressure homogenizer (operated at 10,000 psi) to form a nanoemulsion. The nanoemulsion was hardened by quenching (5-fold dilution in distilled water) to form a nanoparticle suspension, which was then concentrated and purified with distilled water using tangential flow filtration (500 kDa MWCO).

Particle size (z.ave) and the polydispersity index (PDI) were characterized by light scattering, as summarized in Table 1. Drug load was obtained by transferring 1 mL of the nanoparticle suspension to a scintillation vial and drying under vacuum on a rotavap to determine the amount of solids. The drug content was then determined by graphite furnace atomic adsorption spectroscopy (GF-AAS). Encapsulation efficiency was calculated as the ratio between the actual and theoretical drug load. In vitro release was characterized by dialysis of 1 mL of the nanoparticle suspension across a 1000 kDa MWCO membrane in to 60 mL phosphorus buffered saline (PBS) containing 0.1% SLS. The samples were maintained in a shaking water for 48 h at 37° C. and analyzed by GF-AAS.

TABLE 1

Cabazitaxel-platinum(IV) monohexanoate-monosuccinate prodrug conjugate nanoparticle in vitro characterization

| | 40/60% $PLA_{108}/PLA_{35}mPEG_5$ |
|---|---|
| z.ave (nm) | 104 |
| PDI | 0.15 |
| Actual drug load (%) | 10 |
| EE (%) | 5.2 |
| Yield (%) | 52 |
| Release at 24 h (%) | 26 |

EXAMPLE 3

Effect of the Cabazitaxel-Platinum(IV) Monohexanoate-Monosuccinate Conjugate of Formula (II) on a Prostate Carcinoma Cell Line To determine whether a conjugate described herein has an effect on a cancer cell, the cabazitaxel-platinum(IV) monohexanoate-monosuccinate conjugate of formula (II) was tested on the prostate carcinoma cell line DU145 using the Cell-Titer Blue® Cell Viability Assay (Promega, Madison, Wis.).

Cells:

DU145 (ATCC® HTB-81™) cells were obtained from the American Type Culture Collection (ATCC, Manassas, Va.) and aliquots cryobanked until cultured. The cells were rapidly thawed at 37° C.; the contents of the vial were diluted in 10 ml of RPMI-1640 medium containing 10% fetal bovine serum and 2 mM L-Glutamine, and washed by centrifugation (1,200 r.p.m. for 5 minutes, room temperature). The supernatant was discarded and the cell pellet resuspended in 15 ml of complete RPMI-1640 medium and incubated at 37° C., 5% $CO_2$, 95% humidity in a T-75 $cm^2$ flask.

The Compound:

The conjugate of Formula (II) was dissolved in DMSO. The compound stock was diluted two-fold in DMSO to produce a compound master plate (CMP). Aliquots of the working stock solution were subsequently diluted 100-fold in basal RPMI-1640 medium to generate the medium plate. The medium plate was diluted 10-fold to the assay plate containing the cells to provide the appropriate final test concentrations required.

Summary of the Method Used:

DU145 cells were added to a Corning 96-well clear bottom assay plate containing complete RPMI-1640 medium at 2,000 and 5,000 cells per well, respectively, and incubated for 24 hours at 37° C. with 5% $CO_2$ and 95% humidity. Control wells containing no cells were included to measure background fluorescence signal. Following 72 hours of incubation, cell viability was determined using the Cell-Titer Blue Cell Assay according of the manufacturers instructions. Prior to generation of dose response curves, the data were background subtracted using the no cell control values (mean+/–s.d.) and data were plotted using fluorescence values versus $Log_{10}$ concentration of the test compound. The dose response curves were generated using GraphPad Prism 5.0 software.

$IC_{50}$ Determination:

To calculate the concentration of 50% inhibition of colony growth ($IC_{50}$) for each compound, a dose response curve was generated by plotting mean fluorescence values (+/− standard error) versus log of the compound concentration for each test compound. A sigmoidal curve was then fit to the graph and IC50 (μM) was then calculated using a 4 parameter (4PL) algorithm.

$$4(PL)F(x)=(A-D)/(1+(x/c)^B+D$$

where A=lower asymptote (baseline response), D=upper asymptote (maximum response), C=drug concentration that provokes a response halfway between A and D, B=slope of the curve.

Results:

Table 2 shows the results of the $IC_{50}$ of the cabazitaxel-platinum(IV) monohexanoate-monosuccinate conjugate of formula (II) on the prostate carcinoma cell line DU145.

TABLE 2

$IC_{50}$ of Test compound in the DU145 cell line.

| Compound | Log $IC_{50}$ (μM) | $IC_{50}$ (μM) |
|---|---|---|
| Cabazitaxel-platinum(IV) monohexanoate-monosuccinate conjugate of formula (II) | −2.10 | 0.008 |

These data demonstrate that the conjugate compound has activity in reducing tumor cell viability.

The above description of the disclosed embodiments is provided to enable any person skilled in the art to make or use the disclosure. Various modifications to these embodiments will be readily apparent to those skilled in the art, and the generic principles described herein can be applied to other embodiments without departing from the spirit or scope of the disclosure. Thus, it is to be understood that the description and drawings presented herein are representative of the subject matter which is broadly contemplated by the present disclosure. It is further understood that the scope of the present disclosure is not intended to be limited to the embodiment shown herein but is to be accorded the widest scope consistent with the patent law and the principles and novel features disclosed herein.

All references, including publications, patent applications, and patents, cited herein are hereby incorporated by reference to the same extent as if each reference were individually and specifically indicated to be incorporated by reference and were set forth in its entirety herein.

Alternative embodiments of the claimed disclosure are described herein. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the disclosure to be practiced otherwise than as specifically described herein.

Accordingly, this disclosure includes all modifications and equivalents of the subject matter recited in the claims appended hereto as permitted by applicable law. Moreover, any combination of the above described elements in all possible variations thereof is encompassed by the disclosure unless otherwise indicated herein or otherwise clearly contradicted by context.

What is claimed is:

1. A nanoparticle comprising:
   (a) a conjugate comprising

A-Y—Pt wherein:
   Y is a linker;
   Pt is a platinum complex; and
   A is cabazitaxel, a cabazitaxel analogue or a derivative thereof; and
   (b) a base component.

2. The conjugate of claim 1, wherein Y is selected from the group consisting of: $C_1$-$C_{10}$ straight chain alkyl, $C_1$-$C_{10}$ straight chain O-alkyl, $C_1$-$C_{10}$ straight chain substituted alkyl, $C_1$-$C_{10}$ straight chain substituted O-alkyl, $C_4$-$C_{13}$ branched chain alkyl, $C_4$-$C_{13}$ branched chain O-alkyl, $C_2$-$C_{12}$ straight chain alkenyl, $C_2$-$C_{12}$ straight chain O-alkenyl, $C_3$-$C_{12}$ straight chain substituted alkenyl, $C_3$-$C_{12}$ straight chain substituted O-alkenyl, polyethylene glycol, polylactic acid, polyglycolic acid, poly(lactide-co-glycolide), polycarprolactone, polycyanoacrylate, ketone, aryl, heterocyclic, succinic ester, amino acid, aromatic group, ether, crown ether, urea, thiourea, amide, purine, pyrimidine, bypiridine, indole derivative acting as a cross linker, chelator, aldehyde, ketone, bisamine, bis alcohol, heterocyclic ring structure, azirine, disulfide, thioether, hydrazone, and combinations thereof.

3. The nanoparticle of claim 1 wherein Y is selected from the group consisting of: a $C_3$ straight chain alkyl and a ketone.

4. The nanoparticle of claim 1, wherein the conjugate is encapsulated in, tethered to, or associated with the nanoparticle.

5. The nanoparticle of claim 1, wherein the based component is selected from the group consisting of: a polymer, a small molecule, and a mixture thereof.

6. The nanoparticle of claim 5, wherein the nanoparticle may contain a plurality of the same or different conjugates.

7. The nanoparticle of claim 1, wherein the conjugate is a compound of formula II:

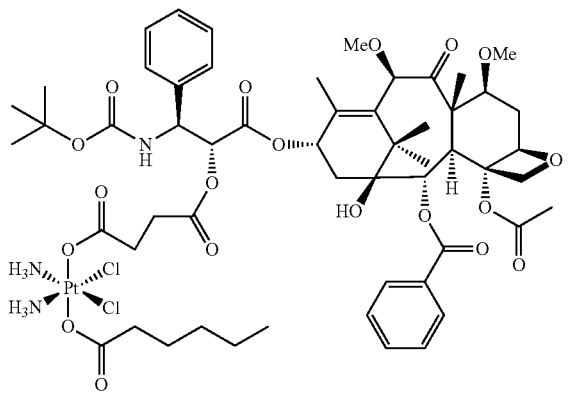

(II)

8. A method of killing a cancer cell, the method comprising contacting a cancer cell with an effective amount of a nanoparticle of claim 1.

9. The method of claim 8, wherein the cancer cell is a prostate cancer cell.

10. A method of treating cancer wherein the cancer is prostate cancer, the method comprising identifying a subject at risk for or diagnosed with prostate cancer and administering a therapeutically effective amount of a nanoparticle of claim 1.

11. The nanoparticle of claim 5, wherein the base component is a polymer comprising polydioxanone (PDO), polyhydroxyalkanoate, polyhydroxybutyrate, poly(glycerol sebacate, polyglycolide, poly(lactic acid) (PLA), polycaprolactone, polylactide, polyglycolide, poly(ortho esters), poly(caprolactones), polylysine, poly(ethylene imine), poly(acrylic acid), poly(urethanes), poly(anhydrides), poly(esters), poly(trimethylene carbonate), poly(beta amino esters), poly(alkylene glycol), or copolymers or derivatives thereof.

12. The nanoparticle of claim 11, wherein the base component is a polymer comprising poly(lactic acid) (PLA), poly(ethylene glycol) (PEG) or copolymers or derivatives thereof.

13. The nanoparticle of claim 5, wherein the base component is a small molecule comprising a lipid.

* * * * *